(12) United States Patent
Kambara et al.

(10) Patent No.: US 6,750,018 B2
(45) Date of Patent: Jun. 15, 2004

(54) METHOD FOR DETECTING NUCLEIC ACID MUTATION BY DETECTING CHEMILUMINISCENCE GENERATED WITH BY-PRODUCT OF COMPLEMENTARY STRAND EXTENSION REACTION

(75) Inventors: Hideki Kambara, Hachioji (JP); Guohua Zhou, Koganei (JP); Kazunori Okano, Shiki (JP); Masao Kamahori, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 164 days.

(21) Appl. No.: 09/945,703

(22) Filed: Sep. 5, 2001

(65) Prior Publication Data

US 2003/0049628 A1 Mar. 13, 2003

(30) Foreign Application Priority Data

Sep. 28, 2000 (JP) ............................. 2000-300577

(51) Int. Cl.[7] .................... C12Q 1/68; C12P 19/34
(52) U.S. Cl. ...................... 435/6; 435/91.1; 435/91.2
(58) Field of Search .................... 435/6, 91.1, 91.2

(56) References Cited

U.S. PATENT DOCUMENTS

| | | | | | |
|---|---|---|---|---|---|
| 4,971,903 | A | * | 11/1990 | Hyman | 435/6 |
| 5,534,424 | A | * | 7/1996 | Uhlen et al. | 435/91.2 |
| 6,210,891 | B1 | * | 4/2001 | Nyren et al. | 435/6 |
| 6,255,083 | B1 | * | 7/2001 | Williams | 435/91.1 |
| 6,258,568 | B1 | * | 7/2001 | Nyren | 435/91.1 |
| 2001/0024790 | A1 | * | 9/2001 | Kambara et al. | 435/6 |

FOREIGN PATENT DOCUMENTS

| | | | | |
|---|---|---|---|---|
| EP | 0 332 435 | * | 9/1989 | C12Q/1/68 |
| WO | 98/55653 | * | 12/1998 | C12Q/1/68 |

OTHER PUBLICATIONS

W. Mathias Howell, Magnus Jobs, Ulf Gyllensten and Anthony J. Brookes, "Dynamic Allele–Specific Hybridization–A new method for scoring single nucleotide polymorphisms", Nature Biotechnology, vol. 17, Jan. 1999, pp. 87–88.

Victor Lyamichev, Andrea L. Mast, Jeff G. Hall, James R. Prudent, Michael W. Kaiser, Tsetska Takova, Robert W. Kwiatkowski, Tamara J. Sander, Monika de Arruda, David A. Arco, Bruce P, Neri, and Mary Ann D. Brow, "Polymorphism Identification and Quantitative Detection of Genomic DNA by Invasive Cleavage of Olignonucleotide Probes", Nature Biotechnology, vol. 17, Mar. 1999, pp. 292–296.

C. R.Newton, A. Graham, L. E. Heptinstall, S. J. Powell, C. Summers, N. Kalsheker, J.C. Smith and A. F. Markham, "Analysis of any point mutation in DNA. The amplification refractory mutation system (ARMS)", Nucleic Acids Research, vol. 17, No. 7, 1989, pp. 2503–2516.

Afshin Ahmadian, Baback Gharizadeh, Anna C. Gustafsson, Fredrik Sterky, Pal Nyren, Mathias Uhlen and Joakim Lundeberg, "Single–Nucleotide Polymorphism Analysis by Pyrosequencing", Analytical Biochemistry 280, pp. 103–110.

* cited by examiner

*Primary Examiner*—Kenneth R. Horlick
(74) *Attorney, Agent, or Firm*—Reed Smith LLP; Stanley P. Fisher, Esq.; Juan Carlos A. Marquez, Esq.

(57) ABSTRACT

To provide a method and an apparatus for detecting DNA mutation without using electrophoresis, the presence or absence of specific sequence is detected by a method comprising a step of serially hybridizing a 5-base-long to 8-base-long short oligomer 6, which is capable of being engaged in the complementary strand extension reaction, and a long oligomer 61, which is capable of hybridizing with a target DNA but incapable of being engaged in the complementary strand extension reaction, with the target DNA 63; a step of carrying out the complementary strand extension reaction 66 starting from the short primer using four kinds of nucleic acid substrates and polymerase; and a step of detecting photo-emission, in which pyrophosphate 68 produced as a reaction by-product of the complementary strand extension reaction is converted into ATP and the photo-emission reaction is carried out using an enzyme.

2 Claims, 11 Drawing Sheets

FIG. 2

| PRIMER | SEQUENCE NUMBER | SEQUENCE | RELATIVE INTENSITY OF CHEMILUMINESCENCE |
|---|---|---|---|
| SNP1-1 | 1 | AGTTTTAAGAGGGTTGTTGT | 100 |
| SNP1-2 | 2 | AGTTTTAAGAGGGTTGTTGC | 65 |
| SNP1-3 | 3 | AGTTTTAAGAGGGTTGTTGG | 61 |
| SNP1-4 | 4 | AGTTTTAAGAGGGTTGTTGA | 6 |
| SNP2-1 | 5 | AGTTTTAAGAGGGTTGTAGT | 97 |
| SNP2-2 | 6 | AGTTTTAAGAGGGTTGTAGC | 3 |
| SNP2-3 | 7 | AGTTTTAAGAGGGTTGTAGG | 5 |
| SNP2-4 | 8 | AGTTTTAAGAGGGTTGTAGA | 4 |

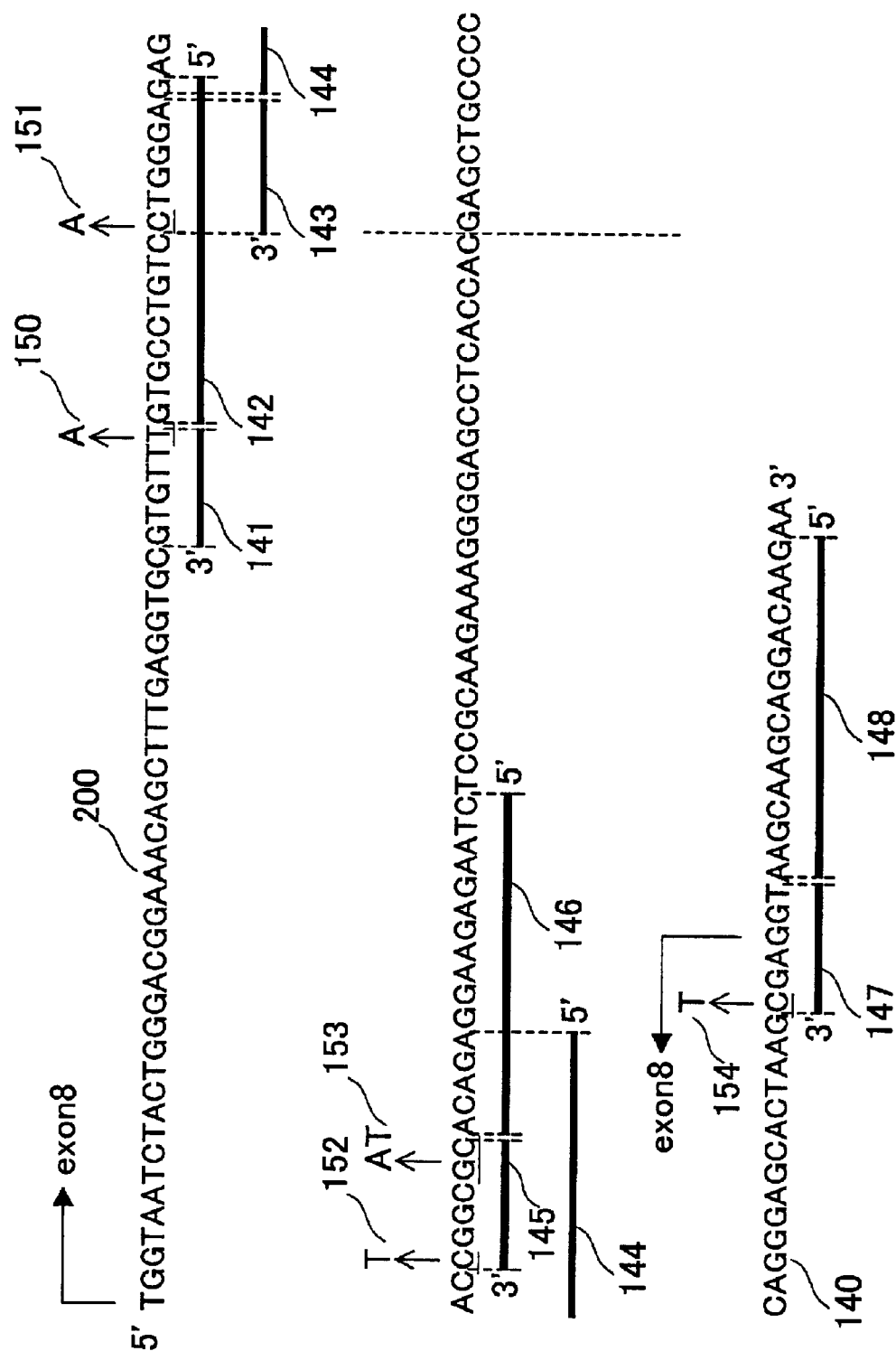

FIG. 12

| SEQUENCE NUMBER | PRIMER OF 6 BASE LENGTH |
|---|---|
| 11' | N A A C A C |
| 12' | T C C C A N |
| 13' | N N G C C N |
| 14' | A C C T C N |

| SEQUENCE NUMBER | DNA PROBES WHICH ARE NOT ENGAGED IN COMPLEMENTARY STRAND EXTENSION REACTIONS |
|---|---|
| 11 | C T C C C A N G A C    A G G C A C |
| 12 | T C T G T N N G C C    N G T C T C |
| 13 | G T T T C T C T T C    C T C T G T |
| 14 | C T T G T C C T G C    T T C G T T |

11' : N=A OR T
12' : N=T OR G
13' : NN AT FIRST AND SECOND POSITIONS FROM 5' TERMINAL IS GC OR AT AND N AT SIXTH POSITION FROM 5' TERMINAL IS G OR A
14' : N=G OR A
11 : N=G OR T
12 : NN AT SIXTH TO SEVENTH POSITIONS FROM 5' TERMINAL IS GC OR AT AND N AT ELEVENTH POSITION FROM 5' TERMINAL IS G OR A

METHOD FOR DETECTING NUCLEIC ACID MUTATION BY DETECTING CHEMILUMINISCENCE GENERATED WITH BY-PRODUCT OF COMPLEMENTARY STRAND EXTENSION REACTION

BACKGROUND OF THE INVENTION

The present invention relates to detection of specific sequences contained in DNAs of test subjects, detection of polymorphisms of genes, analysis of single nucleotide polymorphisms (SNPs), and the like.

The progress of the human genome mapping project is prompting a trend towards applying DNA sequence information to medical diagnoses and various industries, for example, in producing new drugs. Particularly, in a medical field, noticeable is a trend towards revealing and applying gene functions. In particular, analyses of gene expression profiles, in which genes active in a body are examined, and analyses of single nucleotide polymorphisms (SNPs) in genomes, which may be a cause of variations in gene expression, are drawing attention.

In genomes, single nucleotide polymorphisms are said to be present approximately one per 1000 bases, which means every individual has a huge number of single nucleotide polymorphisms. These single nucleotide polymorphisms are considered to be associated with characteristics of individuals so that the analysis of these single nucleotide polymorphisms is expected to provide a therapy guide or the like for the treatment of diseases for the individuals.

The number of single nucleotide polymorphisms present in genomes of one human being is enormous, and the type of single nucleotide polymorphisms in genomes of many people are polymorphic, in which two kinds of bases appear in particular sites. It is necessary to examine single nucleotide polymorphisms occurring at sites of mutation and further to reveal their correlation with diseases or the like, which requires the accumulation of enormous amounts of DNA data. Thus, development of appropriate methods to meet this requirement is in need.

At present, various methods for analyzing base substitutions are available. They are generally divided into two types, i.e., methods for detecting unknown base substitutions and methods for examining, for example, whether certain known base substitutions are found in many people or whether these known substitutions have causal relationships with certain diseases.

Examples of the methods for detecting unknown base substitutions include a method in which a base sequence is determined using a DNA sequencer, and a method in which hybridization of a DNA probe and a target DNA is detected using a DNA probe array (DNA chip or gene chip).

On the other hand, in order to detect single nucleotide polymorphisms at known positions, methods, such as an SSCP (single strand configuration polymorphism) method, an invader assay (Nature Biotechnology, 17, 292–296 (1999)), and DASH (Nature Biotechnology, 17, 87–88 (1999)), have been developed and implemented for practical use. All of these methods use laser or the like as a light source.

In synthesizing a DNA complementary strand using a primer, complementary strand extension may or may not proceed depending on whether the 3'-end of the primer is complementary to the target or not. Accordingly, a method, in which a PCR amplification is performed using a primer having the 3'-end at an accordant position of mutation and products are analyzed using gel electrophoresis or the like (ARMS: amplified refractory mutation system; Nucleic Acids Research, 17, 2503–2515 (1989)), has also been used. In this case, a key point is how exclusively the complementary strand synthesis occurs in the presence of a target of interest.

In the SSCP method, single, nucleotide polymorphisms can be detected based on the observation that the configurations of single-stranded DNAs with and without mutation during electrophoresis are different, and these configurations influence electrophoretic mobility.

In the invader assay, a triple-stranded chain is formed with a DNA probe of a DNA probe array, a target DNA and a DNA probe, and whether a part of the probe is cleaved with an enzyme is detected.

In DASH, a target DNA and a probe DNA are hybridized under the presence of an intercalator, and light generated from the intercalator by irradiation is observed while changing a temperature. The double stranded chain is dissociated and the emission ceases if mutation is present in the target DNA.

On the other hand, anew technique is about to be implemented, in which a short DNA base sequence is determined in a short time and then mutations are examined using the determined DNA base sequence.

For example, Nyren et al. have proposed a method for determining a DNA base sequence (pyrosequencing), in which a target DNA is hybridized with a primer, pyrophosphate produced by a complementary strand extension reaction is converted into ATP, the ATP is reacted with luciferin to emit light, and this chemiluminescence is detected to discriminate the substrate (dNTP) incorporated during the complementary strand extension reaction. The pyrosequencing has drawn an attention as a simple and easy method for determining a DNA sequence without the need for gel electrophoresis. Recently, detection of SNPs using this pyrosequencing has been reported (Anal Biochemistry, 280, 103–110 (2000)). This method does not require the use of a new light source because it utilizes chemiluminescence.

SUMMARY OF THE INVENTION

Mutations which appear in genome DNAs are associated with characteristics of organisms, sensitivity to diseases and medicines, and the like, and thus a huge number of subjects have to be analyzed. Since individuals to be tested are numerous, there is a demand for a method and an apparatus which suit for a simple and large scale operation at a low running cost.

Further, SNP measurements are necessary for individual genome samples, as well as for samples from a patient group and a healthy subject group for comparison. Namely, in order to study a causative relationship between particular SNPs and a certain disease it is necessary to compare the incidence of the SNPs (allele frequency) in the two groups. This comparison study can be most efficiently and easily carried out by combining DNAs of each group and quantitatively analyzing the SNPs contained in the combined DNAs. However, a quantitative method accurate enough for such analyses remains to be developed. Further problems arise upon measurement of SNPs even with individual samples, as described below.

In various methods which have been proposed previously, a targeted DNA region is amplified by PCR and the resulting DNA fragments are used as a target. Accordingly, the use of PCR is inevitable.

In the DASH, it is necessary to use a detector equipped with a laser light source and a filter to remove scattering light, which requires a large-scale apparatus.

In a pyrosequencing for detecting chemiluminescence, pyrophosphate is converted into ATP to generate chemiluminescence and the resulting photo-emission is detected. However, the pyrosequencing has disadvantages such that four kinds of dNTP (dATP, dTTP, dGTP and dCTP) have to be added independently in a designated order to a reaction part, that the photo-emission intensity is weak, that a system for dNTP injection is necessary, and that a considerably large-scale apparatus is required.

Further problems in this method are that because reagents are injected in a designated order, the time required for the analysis is 10–20 minutes although it is shorter than that with the use of electrophoresis, and that sample DNAs have to be PCR-amplified to increase the number of DNA copies of the target region because the method is not sensitive enough without amplification.

Furthermore, in pyrosequencing, if a multiple number of base substitutions exist in a sample to be tested, the resulting spectrum may be too complicated to perform accurate analyses.

In order to apply the pyrosequencing for the detection of DNA mutations, it is important to further improve the sensitivity so that the DNA mutations can be readily detected and DNA strands containing multiple kinds of mutations can be analyzed.

An object of the present invention is to provide a tool necessary to create a data base applicable for genetic diagnoses, new drug manufacturing using genes, and gene therapies, and further to provide a method, an apparatus, test reagents and the like for examining gene DNAs.

More specifically, an object of the present invention is to provide a highly sensitive, easy method and an apparatus for detecting DNA mutations, in which the use of excitatory light source is not necessary and the reaction is simple and quick, and further to provide a method and an apparatus for detecting DNA mutations, in which a sample containing multiple mutations can be analyzed at a high reliability.

Another object of the present invention is to provide a technique for readily screening interrelations between a certain disease and SNPs.

In the present invention, in order to examine the presence or absence of a target DNA of interest, or the presence or absence of mutations, a DNA probe (primer) capable of being engaged in complementary strand extension is hybridized with the target DNA, pyrophosphate generated as a result of the complementary strand extension reaction is converted into ATP to emit light, and this photo-emission is detected. When the target DNA sequence is not present in the test sample, the complementary strand extension does not take place so that no photo-emission is observed.

Further, in the present invention, probes are prepared to have the 3'-end base at a position accordant to mutations and have different 3'-end sequences so that the complementary strand extension reaction occurs only if mutation exists or the complementary strand extension reaction does not occur only when mutation exists. Thus, this method can be used also for detecting mutations. This is because the complementary strand extension reaction starting from the primer highly depends on whether the hybridization matching at the 3'-ends is perfect or imperfect (Kwok S. et al., Nucleic Acids Res., 18, 999–1005 (1990); Huang M. M., Arnhein N., Goodman M. R., Nucleic Acids Res., 20, 4567–4573 (1992)).

In order to accurately switch on/off of the primer complementary strand extension reaction in response to a DNA template for targeted SNP measurements, an artificial mismatch is introduced near the 3'-end of the primer. The presence or absence of the complementary strand synthesis is examined by converting the produced pyrophosphate into ATP, reacting the ATP with a chemiluminescent reagent and optically detecting the resulting chemiluminescence. In order to accomplish a highly accurate detection by this method, pyrophosphate contained as an impurity and pyrophosphate resulting from heat decomposition of nucleic acid substrates, which generate a background light, are minimized as much as possible, and at the same time, the chemiluminescence resulting from the complementary strand extension is detected using two primers having the end bases complementary to a wild type and a mutant.

In a conventional pyrosequencing, photo-emission intensity is weak because the photo-emission uses pyrophosphate resulting from a complementary strand extension reaction with only one base. Contrastingly in the present invention, the complementary strand extension reaction proceeds with more than dozens of bases and chemiluminescence is detected by converting the resulting pyrophosphate into ATP so that the photo-emission intensity is more than two orders stronger than that attained by the conventional pyrosequencing.

Further, it is possible to enhance the photo-emission intensity by repeating the decomposition of the double-stranded chain resulting from the complementary strand extension reaction using an enzyme and the process of the complementary strand extension. Thus, the presence or absence of specific sequences or mutations, and the ratio of mutation contained in combined genome samples can be detected without PCR-amplification of the samples.

In the present invention, substrates for the complementary strand synthesis, i.e., dNTPs, are added in a controlled manner upon the complementary strand extension starting from a primer, pyrophosphate produced in response to the complementary strand extension reaction is detected by chemiluminescence emission, and thus the presence or absence of base mutations and the presence of a wild type and a mutant in a target DNA are detected. The presence or absence of substitution of base sequences or base mutation can be examined by a simple and highly sensitive method using primers designed such that their 3'-ends come to the position of the anticipated base substitution in the target DNA and the complementary strand extension may or may not occur depending on the presence or absence of the substitution.

When the complementary strand extension occurs, multiple dNTPs are simultaneously added to proceed the complementary strand extension all the way through and produce a large amount of pyrophosphate so that the intensity of chemiluminescence can be enhanced to attain a highly sensitive detection of base mutations.

Multiple primers are prepared taking the sequence of a target DNA into consideration, and the progress of complementary strand extensions starting from these various primers are detected to discriminate the presence of multiple kinds of mutations. Further, multiple-kinds of base substitutions can be analyzed with high reliability by sorting and holding multiple primers for the reaction according to known standard DNA sequences. When a sample contains various mutants, multiple primers are prepared referring to the standard base sequence and immobilized on a solid surface by kind, and complementary strand extension reactions are carried out using these primers to monitor the presence of mutants.

An analysis of test samples containing various mutations has been extremely difficult with conventional methods. However, the mutations can be detected using a simple method and an apparatus according to the present invention.

BRIEF DESCRIPTION OF THE DRAWINGS

FIG. 2 illustrates examples of the structures of primers used in Example 1 and relative photo-emission intensities in response to the formation of extended complementary strands by respective primers.

FIG. 11 illustrates Example 5.

FIG. 12 shows the structures of probes incapable of being engaged in the complementary strand extension reaction and 6-base-long primers for detecting mutations shown in FIG. 11.

DESCRIPTION OF THE PREFERRED EMBODIMENT

Figure 1A:
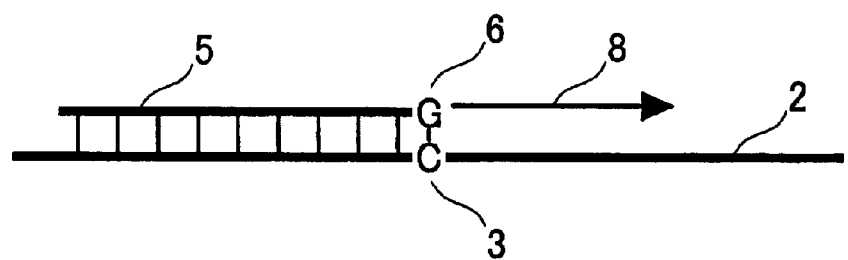
FIG. 1a illustrates a first stage of a hybridization process, wherein the base at the 3'-end 6 of the primer 5 and the base C at the position 3 are complementary.

Examples of the present invention will be hereinafter explained in detail referring to the attached drawings.

First, a photo-emission mechanism, the premise of the present invention, will be explained referring to a related technique, pyrosequencing. A primer is hybridized with a target DNA. DNA polymerase and dNTPs, substrates for a complementary strand synthesis in a complementary strand extension reaction, are added to proceed the complementary strand extension reaction. Substrates complementary to the DNA strand are incorporated one by one and the complementary strand is extended by DNA polymerase. At the same time, pyrophosphate is produced as a reaction by-product. One molecule of pyrophosphate is produced every time when one dNTP is incorporated.

Pyrophosphate is converted into ATP by sulfurylase and the resulting ATP oxidizes luciferin in the presence of luciferase to emit light. Progress of the complementary strand extension starting from the primer can be monitored by detecting this photo-emission. Four kinds of dNTP are added one by one in a designated order to a reaction part. The photo-emission with an added dNTP implies the incorporation of this particular dNTP, whereby a DNA sequence is determined.

At this case, it is necessary to decompose excess dNTPs so that the succeeding reaction is not interfered. An addition of apylase is reported as an essential technique (Science, 281, 363–364 (1998)). In this case, the photo-emission intensity decreases by one order by the addition of apylase since apylase also decomposes ATP and thus the photo-emission reaction and the decomposition reaction occur competitively. The sequencing using this reaction requires about 0.2 pmol of target DNA.

The method of the present invention largely differs from the conventional pyrosequencing in that a primer for the complementary strand extension is designed to have the 3'-end or the vicinity of the 3'-end at the position complementary to a position of mutation upon hybridization with the sample. A DNA strand portion which is engaged in the complimentary strand synthesis does not contain a complementary portion at the position of mutation. Furthermore, the method of the present invention is characterized in that the complementary strand synthesis is proceeded by successive incorporation of multiple bases, a large number of the resulting pyrophosphate react with a chemiluminescence reagent to generate chemiluminescence for highly sensitive detection without the need for recognizing the extending DNA sequence. Furthermore, the method of the invention is characterized in that in order to obtain more accurate SNP information or quantitative mutant information, the complementary strand synthesis is carried out using two kinds of primers having the end bases in accord with complementary bases of mutant and wild type DNAs to ultimately measure chemiluminescence.

EXAMPLE 1

FIGS. 1(a) through (d) are drawings to illustrate Example 1 showing that the hybridization proceeds completely or incompletely depending on the kind of the base at the 3'-end of the primer, and thus the complementary strand synthesis is controlled.

A single-stranded target DNA 1 is prepared from a DNA containing mutation, and a single-stranded target DNA 2 is prepared from a DNA without mutation. In this example, two different DNAs having a base length of about 400 are used; longer DNAs can also be used without any difficulty. The target DNAs 1 and 2 are hybridized with a 10-base-long primer 5 in which the base at the 3'-end 6 is designed to be in accord with the base at a position 3 of the target DNAs 1and 2, where the presence or absence of mutation is to be examined. The complementary strand extension reaction is carried out by adding DNA polymerase and substrates for the complementary strand synthesis, i.e., dATP, dTTP, dGTP and dCTP. The primer shown in FIG. 1 is 10 base long; however, primers having a base length of 10 to 30 are generally used.

In the example shown in FIG. 1(a), the base (G) at the 3'-end 6 of the primer 5 and the base (C) at the position 3, where the presence or absence of mutation of the target DNA 2 is to be examined, are complementary, so that substrates complementary to the DNA strand are successively incorporated by DNA polymerase to form the extended complementary strand as indicated with the arrow 8. As a result, pyrophosphate is produced as a reaction by-product.

Figure 1B:
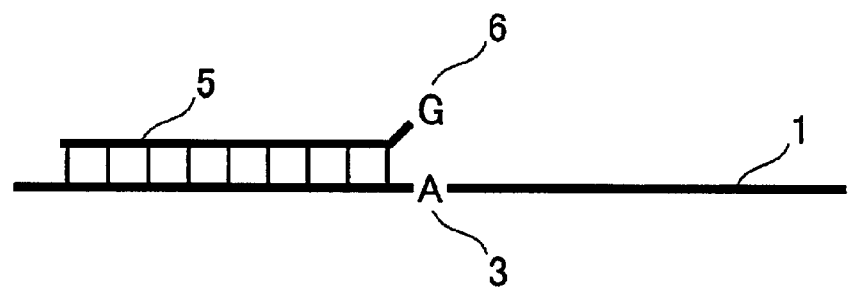
FIG. 1b illustrates a first stage of a hybridization process, wherein the base at the 3'-end 6 of the primer 5 and the base C at the position 3 are not complementary.

In the example shown in FIG. 1(b), the base (G) at the 3'-end 6 of the primer 5 and the base (A) at the position 3 of the target DNA 1, where the presence or absence of mutation is to be examined, are not complementary. Accordingly, substrates complementary to the DNA strands are hardly incorporated by DNA polymerase so that the complementary strand extension hardly occurs. As a result, the amount of pyrophosphate produced as a reaction by-product is small.

As described above, pyrophosphate is detected using photo-emission by luciferase. Strong signals are detected in the example shown in FIG. 1(a), but not in the example shown in FIG. 1(b).

However, the strand extension may occur with some targets at a considerably high probability even if bases at their 3'-ends are not complementary.

Therefore, a primer 9 is used instead of the primer 5 in order to detect mutation more accurately, or to switch the complementary strand synthesis more accurately in response to the kind of end bases. The sequence of the primer 9 is the same as that of the primer 5 except that the base at the second or third base position from the 3'-end 6 of the primer 5 is replaced by the base (A) which is not complementary to the corresponding base of the target DNAs 1 and 2.

The third base from the 3'-end of the primer 9 shown in FIGS. 1 (c) and 1(d) is the base (A) which is not complementary to the corresponding base (C) of the target DNAs 1 and 2, which generate an artificial mismatch at the third base from the 3'-end 6. As a consequence, the 3'-end 6 of the primer 9 is detached from the target DNA when the 3'-end 6 of the primer 9 is mismatched. Thus, the complementary strand extension reaction of the 3'-end of the primer 9 is sensitively affected by the presence or absence of the mismatch.

Figure 1C:
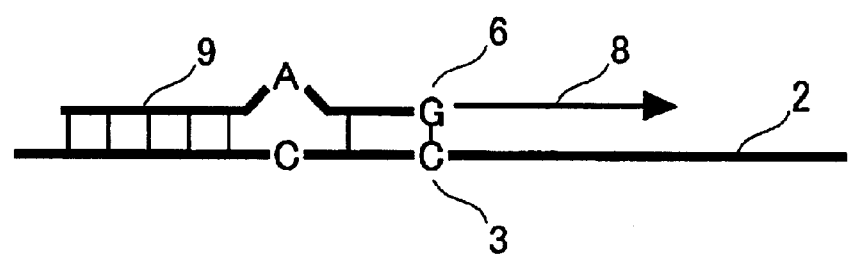
FIG. 1c illustrates an example of a hybridization process, wherein the base G at the 3'-end 6 of the primer 9 is complementary to the base C at the position 3 of the target DNA 1, where the presence or absence of mutation is examined.

In the example shown in FIG. 1(c), the base (G) at the 3'-end 6 of the primer 9 is complementary to the base (C) at the position 3 of the target DNA 1, where the presence or absence of mutation is to be examined. In this case, even if the artificially mismatched base (A) at the third base from the 3'-end 6 of the primer 9, where the presence or absence of mutation of the target DNA 1 is to be examined, is not complementary to the base at the corresponding position of the target DNA 2, substrates complementary to the DNA strand are successively incorporated by DNA polymerase to form the extended complementary strand 8. As a result, pyrophosphate is produced as a reaction by-product.

Figure 1D:
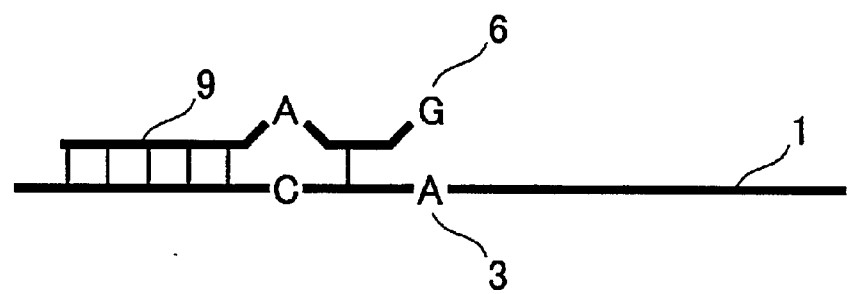
FIG. 1d illustrates an example of a hybridization process, wherein the base G 6 at the 3'-end of the primer 9 is not complementary to the base A at the position 3 of the target DNA 1, where the presence or absence of mutation is examined.

In contrast, in the example shown in FIG. 1(d), the base (G) 6 at the 3'-end of the primer 9 is not complementary to the base (A) at the position 3 of the target DNA 1, where the presence or absence of mutation is to be examined. In this case, the complementary strand extension reaction hardly occurs so that no extended complementary strand will be formed when the additional mismatch exists at the 3'-end of the primer 9, since the artificially mismatched base (A) at the third base from the 3'-end 6 of the primer 9, where the presence or absence of mutation of the target DNA 1 is to be examined, is not complementary to the base at the corresponding position of target DNA 2. As a result, pyrophosphate is not produced as a reaction by-product. Although in both FIGS. 1(b) and 1(d) no complementary strand is shown to be extended from the 3'-end 6 where the presence or absence of mutation of the target DNA 1 is to be examined, complementary strand extension may occur with certain target base sequences in the case of FIG. 1(b). For example, FIG. 2 shows the probability (frequency) of complementary strand extension using various primers. Relative photo-emission intensities for primers having mismatch-rendering bases (changes) at their ends are shown while a photo-emission intensity obtained using a primer SNP1-1, which has a completely complementary sequence, is set to be 100. The figures show that the complementary strand extension occurs at a considerably high probability even in the presence of mismatch-rendering end bases. On the other hand, in FIG. 1(d), an artificial mismatch is introduced at the third base from the 3'-end. As a consequence, the complementary strand extension is more securely suppressed since two mismatches altogether exist in the vicinity of the end. In fact, this suppression is shown in FIG. 2 as the photo-emission intensity obtained by using primer SNP 2-i (i=1 through 4). The photo-emission intensity obtained using the primer SNP 2-1 having a match at the end is almost the same with that obtained using the completely matched primer (SNP 1-1). However the photo-emission intensity is extremely weak if a mismatch is introduced at the end and the resulting figures are almost the same as that attributable to impurities contained in reagents. Namely, the complementary strand synthesis hardly occurs when at least two mismatches are present in the vicinity of the end. Further, a similar reaction occurs by using a primer which introduces a mismatch at the end of the primer while a site of the primer corresponding to the position of mutation is set to be the third base from the end. Namely, in FIG. 1(d), in contrast to the structure in FIG. 1(b), the complementary strand extension is more securely suppressed by making the primer 9 not complementary at the third base from the 3'-end 6 where the presence or absence of mutation of the target DNA 1 is to be examined and at the 3'-end 6.

As explained above, ATP and luciferin are reacted using luciferase to emit light and the resulting photo-emission is detected to examine mutations. Namely, mutation is detected in the example shown in FIG. 1(c), but not in the example shown in FIG. 1(d).

FIG. 2 shows examples of the structure of the primer 5 and primer 9 and the photo-emission intensity in response to the formation of the extended complementary strand by each of these primers.

For the primer 5, the following four kinds of primers (name of the primers: SPN 1-i; i=1, 2, 3, and 4) having different bases at the 3'-end are used for evaluation. Each of the primer SPN 1-i (i=1, 2, 3, and 4) is a 20-base-long sequence, i.e., Sequence Identification Number (SEQ ID NO:) 1, 2, 3, or 4.

AGTTTTAAGA GGGTTGTTGT (SEQ ID NO: 1)
AGTTTTAAGA GGGTTGTTGC (SEQ ID NO: 2)
AGTTTTAAGA GGGTTGTTGG (SEQ ID NO: 3)
AGTTTTAAGA GGGTTGTTGA (SEQ ID NO: 4)

For the primer 9 (SPN 2-i (i=1, 2, 3, or 4)), the following four kinds of primers (name of the primers: SPN 2-i, i=1, 2, 3, and 4) which are the same with the primer 5 except that the third base from the 3'-end of the primer 5, i.e., T, is replaced by A are used for evaluation. Each of the primer SPN 1-i (i=1, 2, 3, and 4) is a 20-base-long sequence, i.e., Sequence Identification Number (SEQ ID NO:) 5, 6, 7, or 8.

AGTTTTAAGA GGGTTGTAGT (SEQ ID NO: 5)
AGTTTTAAGA GGGTTGTAGC (SEQ ID NO: 6)
AGTTTTAAGA GGGTTGTAGG (SEQ ID NO:-7)
AGTTTTAAGA GGGTTGTAGA (SEQ ID NO: 8)

One of the results of the test in which sample DNAs having various mutations were practically used will be explained as follows.

FIG. 3 illustrates an example of detecting a target DNA having a mutation, showing the relative photo-emission intensity by luciferase, which shows the presence or absence of pyrophosphate produced as a reaction by-product in response to the complementary strand extension reaction according to the primers.

The target DNA has a mutation and have a 20-base-long sequence, SEQ ID NO: 9. The base Cat the end of the base sequence shown in SEQ ID NO: 9 is replaced by A by mutation.

TCAAAATTCT CCCAACAACA (SEQ ID NO: 9)

Figure 3A:
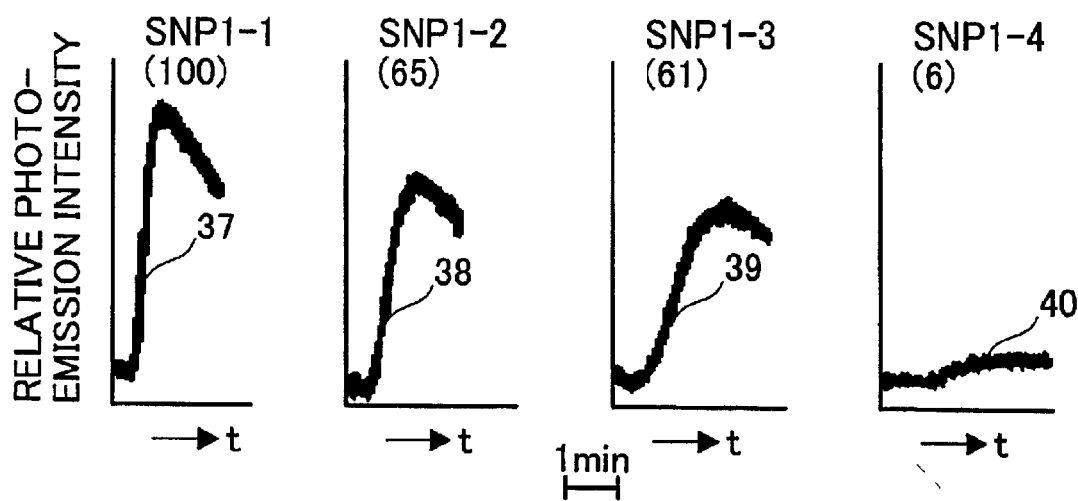
FIG. 3 illustrates examples of detecting target DNAs having mutations, in which relative photo-emission intensity by luciferase is shown to indicate the presence or absence of pyrophosphate produced as a reaction by-product upon the complementary strand extension reaction in response to primers.
Figure 3B:
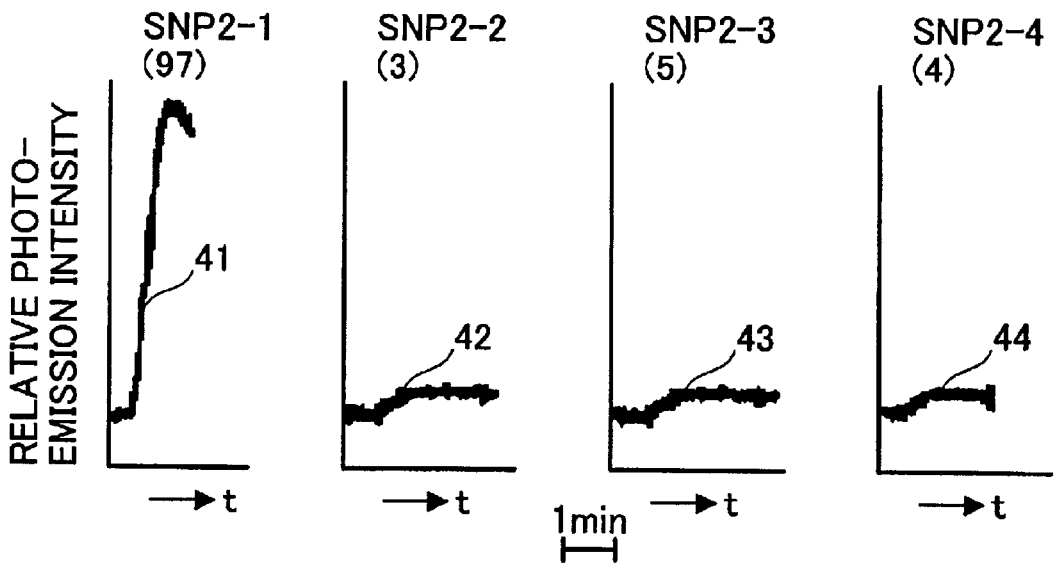

FIG. 3(a) shows the relative photo-emission intensity obtained by using the primer 5 (primer SPN 1-i (i=1, 2, 3, or 4)) in which no artificial mismatch is introduced into the third base from the 3'-end. FIG. 3(b) shows the relative photo-emission intensity obtained by using the primer 9 (primer SPN 2-i (i=1, 2, 3, or 4)) in which an artificial mismatch is introduced into the third base from the 3'-end. The vertical axis shows the relative photo-emission intensity setting the photo-emission intensity obtained by using SPN1-1 to be 100. Figures in parentheses below the names of primers, i.e., SPN1-i (i=1, 2, 3, or 4) and SPN 2-i (i=1, 2, 3, or 4), are relative photo-emission intensities. The relative emission intensities shown in FIG. 2 are these figures.

The horizontal axis shown in FIGS. 3(a) and 3(b) shows the time elapsed for the change in the relative photo-emission intensity. The scale shown below the axis indicates one minute. DNA polymerase and substrates for the complementary strand synthesis, i.e., dATP, dTTP, dGTP and dCTP, are added to a buffer solution containing the target DNA and primers at the time corresponding to the starting point of each curve showing the relative photo-emission intensity, i.e., curves 37, 38, 39, 40 and curves 41, 42, 43, and 44, to start the complementary strand extension. Figures show that the reaction proceeds with the time elapsed.

As shown with curves 37 through 40 in FIG. 3(a), as for the primer 5 with no artificial mismatch introduced (primer SPN 1-i (i=1, 2, 3, or 4)), the curve 37 for the complementary strand extension using primer SPN 1—1 cannot be clearly distinguished from the curves 38 and 39 for the complementary strand extension using primers SPN 1-i (i=2 and 3, respectively). Namely, the complementary strand extension proceeded in spite of the fact that the bases of the 3'-end of primers SPN 1-2 and SPN 1-3 mismatch with the base of the target DNA in the corresponding position. Of course, the photo-emission with primers SPN 1-2 and SPN 1-3 are weaker than that with SPN 1—1 so that they are not entirely be undistinguishable. However, mutant and wild type cannot accurately distinguished and their ratio in a sample cannot be accurately estimated.

On the other hand, as shown with curves 41 through 44 in FIG. 3(b), as for the primer 9 (primer SPN 1-i (i=1, 2, 3, or 4)) in which an artificial mismatch is introduced into the third base from the 3'-end, the selectivity of primers is improved. Namely, while the photo-emission with primer SPN 2-1 shown with the curve 41 is similar to that shown with the curve 37, the photo-emission is hardly detected with primers SPN 2-i (i=2, 3, and 4) as shown with curves 42, 43, and 44.

Thus, the mutation in the base sequence can be more accurately detected by using the primer 9 (primer SPN 2-i (i=1, 2, 3, or 4)) in which a mismatch is artificially introduced into the third base from the 3'-end.

In FIGS. 3(a) and 3(b), the curves 37, 38 and 39 for the primers 5 (SPN 1-i (i=2, 3 and 4)) and the curve 41 for the primer 9 (SPN 2-1) show that about 400 complementary strands are synthesized by the complementary strand extension reaction and that the photo-emission intensity reaches at its peak and then declines. The photo-emission detected here results from chemiluminescence emission with pyrophosphate released by the complementary strand extension reaction.

Figure 3C:
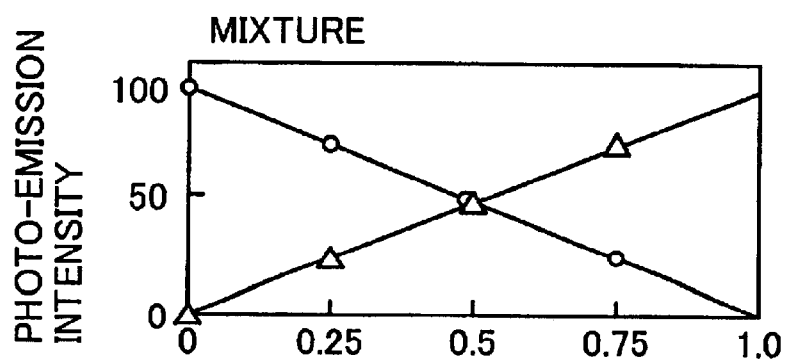
Figure 4A:
FIG. 4 illustrates the outline of chemical reactions in Examples of the present invention.
Figure 4B:
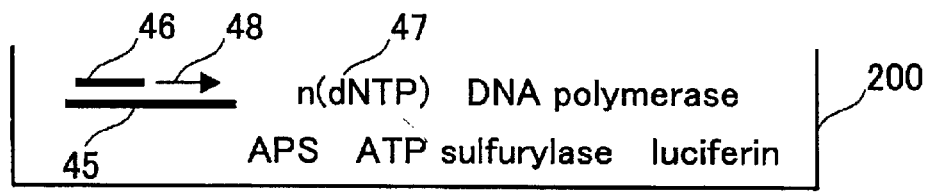
Figure 4C:
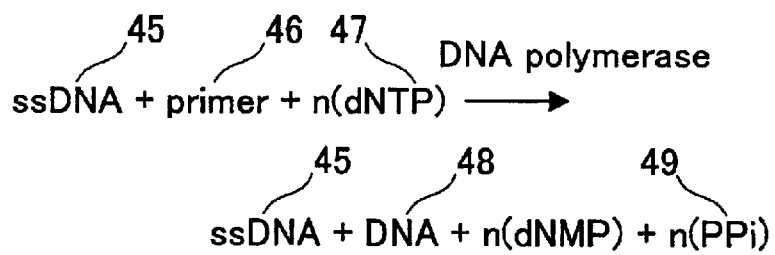
Figure 4D:
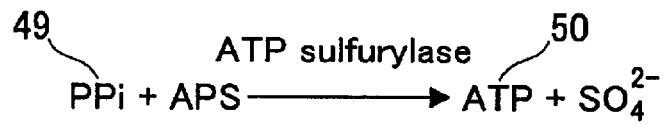
Figure 4E:

In order to detect SNPs more accurately or to estimate the ratio of those SNPs in a sample in which wild type and mutant genes coexist, at least two kinds of primers which are most suitable to each of the genes are to be used. In this case, primer SNP 2-1 and SNP 2-3 are used since mutation occurs in a form of C/A. SNP 2-1 is hybridizable with the mutant sequence, but not with the wild type sequence, to proceed the complementary strand synthesis. On the other hand, SNP 2-3 is hybridizable with the wild type sequence, but not with the mutant sequence, to proceed the complementary strand synthesis. The photo-emission intensity observed upon hybridization with the mutant sequence shown in Table is the background light derived from impurities and pyrophosphate produced by decomposition of nucleotide substrates (dNTPs), and becomes zero by background adjustment. It is important to know the ratio of the wild type and mutant in a genome mixed samples or the like, which contain both the wild type and mutant sequences. In particular, in order to study relationship between diseases and SNPs, it is important to compare the incidence of SNPs of interest in genomes of patients and in healthy subjects. For that, it is necessary to analyze SNPs in an extremely large number of samples. A huge number of data have to be obtained since SNPs are numerous. In such a case, a correlation with a certain disease can be efficiently examined by measuring SNPs in pooled genomes of patients and pooled genomes of healthy subjects. Generally, the significance level for the incidence of SNPs is considered to be more than 1% and the significance level for the correlation with disease is considered to be more than 5%. Therefore, in a mixed genome sample, the ratio of the incidence of SNPs has to be measured at the accuracy level of about 1%, which has been difficult using conventional methods. According to a method of the present invention, the ratio of the incidence can be determined at the accuracy level of about 1% by measuring the ratio of respective complementary strand extensions using two primers. FIG. 3(c) shows the result of the experiment discussed above. Namely, FIG. 3(c) shows results of measurement for a mixed genome sample containing both the wild type and mutant, according to the present invention.

The horizontal axis of FIGS. 3 (c) is the presence ratio of mutation while maintaining the sum of wild type and mutant to be constant. The signal intensity derived from wild type (open circle) and the signal intensity derived from mutant (open triangle) are shown. The reaction for the measurement was carried out using primers each specific to wild type and mutant sequences. As the results show, when the ratio of the mutant increases, the photo-emission intensity for the wild type decreases and that for the mutant increases. Taking the S/N ratio into consideration, detection is possible when the ratio of mutation is as low as about 1%. It is evident that a sufficiently accurate detection is possible according to the invention since the significant level of detection ratio necessary to determine the correlation between normality and disease is 5%, as described above.

In order to improve the accuracy of measurement, it is effective to detect SNPs using the total of four kinds of primers for both double-stranded DNAs.

FIG. 4 explains the outline of the chemical reactions in Example 1 of the present invention. In FIG. 4(a), a target DNA 45 and a primer 46 are introduced into a buffer solution in a reaction vessel 200. In FIG. 4(b), DNA polymerase and substrates for complementary strand synthesis, i.e., dNTPs (dATP, dTTP, dGTP and dCTP) are added to the buffer solution in the reaction vessel and the complementary strand extension proceeds as shown with an array 48. At this time, APS (adenosine 5'-phosphosulfate), ATP sulfurylase and luciferin are also added. FIG. 4(c) shows chemical reactions in the case where the complementary strand extension proceeds, in which as a result of the reaction with DNA polymerase on the target DNA 45, the primer 46 and the substrates, unreacted target DNA 45, a double-stranded DNA synthesized with the extended complementary strand 48 and the target DNA 45, and pyrophosphate (PPi) 49 are obtained. The number of molecules of the resulting pyrophosphate (PPi) 49 is equivalent to that of dNTP 47 incorporated in proportion to the base length upon the synthesis of the extended complementary strand 48. In FIG. 4(d), each molecule of resulting pyrophosphate (PPi) 49 is converted into ATP 50 by ATP sulfurylase in the presence of APS. At the same time, sulfuric acid ion is produced. In FIG. 4(e), the converted ATP 50 oxidizes luciferin in the presence of luciferase to emit light (hî) 51. At this time, carbon dioxide is produced, pyrophosphate is converted into ATP and the ATP oxidizes luciferin to produce pyrophosphate (PPi) 49'. The PPi 49' is again converted into ATP 50 by ATP sulfurylase and the ATP reacts with luciferin. If the complementary strand extension proceeds up to a 400 base length, 400 molecules of pyrophosphate 49 are to be produced by the complementary strand extension reaction for one target DNA. The reaction converts ATP into AMP (adenosine monophosphate) and pyrophosphate. The pyrophosphate is again converted into ATP and thus the emission reaction is repeated to continue the emission.

As evident from the data on the photo-emission intensity obtained in FIG. 3, the reaction for ATP production after the complementary strain extension reaction transitionally continues as long as sufficient APS, luciferin and O2 are present, whereby the emission reaction further continues and the emission 51 is maintained. The photo-emission intensity 51 is proportional to the amount of produced pyrophosphate 49, i.e., the length of DNA chain of the extended complementary stand 48.

In this Example 1, the mixture of all four kinds of substrates for the complementary strand synthesis, i.e., dNTPs 47 (N=A, T, G and C), can be put along with DNA polymerase into the reaction solution containing the single-stranded target DNA 45 and the primer 46. Therefore, this method can attain a highly sensitive detection by obtaining chemiluminescence having intensity as high as double digits as compared to the pyrosequencing in which DNA sequencing is carried out by a step-by-step reaction. In the pyrosequencing, substrates dNTP (N=A, T, G and C) for the complementary strand synthesis must be added independently by kind in a designated order into the reaction part.

Figures 5A, 5B:
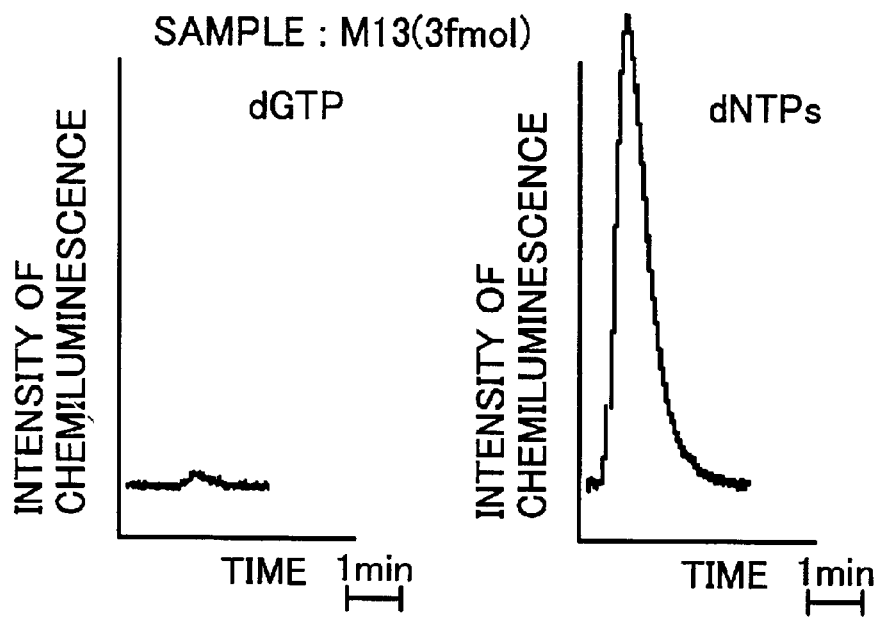
FIG. 5 shows the comparison of the photo-emission intensity in the complementary strand extension reaction by a conventional pyrosequencing with the photo-emission intensity in the complementary strand extension reaction by the method in Example 1.

FIG. 5(a) shows the comparison of the photo-emission intensity obtained by pyrosequencing (a graph marked with dGTP) and the method of Example 1 (a graph marked with dNTP) in which the primer 9 (with an artificial mismatch) shown in FIG. 2 is bound to a single-stranded target DNA. In pyrosequencing, only one kind of substrate dNTP or ddNTP (dideoxy nucleotide triphosphate) (N=either one of A, T, G and C) is used to proceed the complementary strand extension for only one base. In the method of Example 1, all four kinds of substrate dNTPs (N=A, T, G and C) are added simultaneously to proceed the complementary strand extension over a broad region. A sample used is 3 fmol of M13. FIG. 5(b) shows background data obtained under the same conditions as those for FIG. 5(a) except that no sample is added.

In this example, since apyrase is added in the sample to decompose ATP and pyrophosphate, emission and decomposition compete. As a result, the emission intensity is low and cannot be maintained. Background emission is generated because pyrophosphate is often contained in sample DNAs, enzymes, dNTP and ddNTP, as an impurity. Such pyrophosphates can be decomposed by adding apyrase and the background emission disappears. If these contaminating pyrophosphates are removed in advance, the level of the signal intensity several times higher than the peak value can be maintained and there is no need for adding apyrase.

In FIG. 5(a) and FIG. 5(b), the vertical axes indicate photo-emission intensity and the horizontal axes indicate the time elapsed for the photo-emission intensity. FIG. 5(a) shows that the photo-emission intensity obtained by the complementary strand extension using four kinds of substrates dNTP to release an abundant pyrophosphate for chemiluminescence generation is about 50 times higher than that obtained by extension of only one base using only one kind of dGTP. This comparison also shows that the sensitivity can be highly improved by the method of this Example 1.

More specifically, if the background data in FIG. 5(b) is taking into consideration, the sample DNA (M13) cannot virtually be detected when only dGTP is added, since the signal intensity in FIG. 5(a) and background data in FIG. 5(b) are equivalent. In contrast, when four kinds of dNTP are added, the signal intensity in FIG. 5(a) is 12 times higher than that of the background data in FIG. 5(b). In fact, one DNA base mutation can be detected at the order of 10–18 mol since the measurement noise was $1/78$ signal intensity. This signal level is considered to be sufficient for the detection without PCR amplification.

Pyrophosphoric acid contained in samples or phosphoric acid generated from the decomposition of dNTP or ddNTP are responsible for the background emission which may thus interfere the measurement of such a trace amount of DNA. These phosphoric acids were removed by treating reagents to be used in the reaction in advance with apyrase to reduce the background light.

EXAMPLE 2

Example 2 is an example in which two adjacent DNA primers are used like a single primer. Namely, two adjacent primers, long and short, are hybridized with a target DNA instead of introducing a mismatch in a primer itself like the primer 9 shown in FIG. 2. This method is based on the observation that a short primer is difficult to hybridize if a mismatch is present.

FIG. 6 illustrates Example 2. In Example 2, two probes placed side by side act like a single primer; the first probe is long enough to stably hybridize with a target DNA and the second probe is too short to hybridize and synthesize a complementary strand by itself but becomes hybridizable with the target DNA when placed closely adjoining to the 3'-end of the first probe. FIG. 6 exemplifies the detection of mutation, in which the complementary strand extension reaction is carried out starting from the 3'-end of the second probe of a nominal primer, in which the 3'-end of the first primer and the 5'-end of the second probe are closely adjoined, and the photo-emission is detected using luciferase.

Figure 6A:
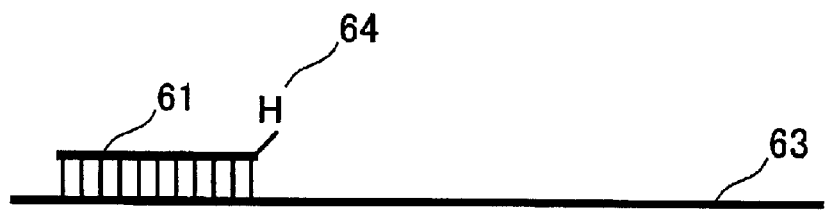
FIG. 6 illustrates Example 2.

As shown in FIG. 6(a), the first probe 61 is 15 to 30 bases long, which is long enough to stably hybridize with a single-stranded target DNA 63. The 3'-end of the first probe is made to be dideoxynucleotide 64 to prevent complementary strand extension, since the first probe hybridizes with any target DNA regardless of the presence or absence of SNPs.

In another method, a short oligomer and a long oligomer are first hybridized in a series. Then, they are bound by a ligation reaction. For this reaction, a short oligomer complementary to a wild type sequence and a short oligomer complementary to a mutant sequence are prepared. The 3'-end of the oligomer complementary to the wild type is made to be dideoxynucleotide so as not to proceed the complementary strand extension. The oligomers ligate and the complementary strand extension proceeds only when the sample is mutant. However, the extension does not occur if the sample is wild type. In this way, the wild type and the mutant can be distinguished.

Figure 6B:
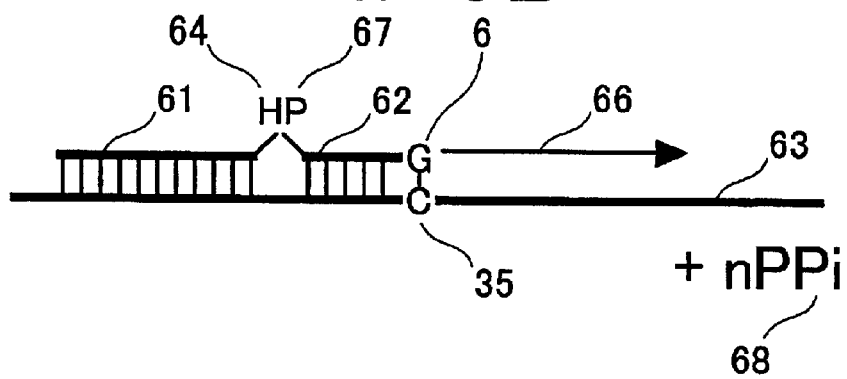

As shown in FIG. 6(b), the second probe 62 having 5 or 6 bases, which is placed closely adjoining to the 3'-end of the first probe 61, hybridizes with the target DNA 63. The 5'-end of the second probe 62 is made to be phosphoric acid group 67 which readily adheres to the 3'-end of the first probe 61. The 3'-end of the second probe 62 can be a start of the complementary strand synthesis but the probe is made too short to proceed the complementary strand synthesis by itself although it is hybridizable.

The second probe 62 can stably function as a primer only when it is adjoined close to the first probe 61 and hybridized with the target DNA. In the method of Example 2, only when the first probe 61 and the second probe 62 hybridize with the target DNA 63, an extended complementary strand 66 having n bases is formed and n molecules of pyrophosphate 68 are generated. Namely, a high selectivity can be attained by the hybridization of the two closely adjoined probes with the target DNA. Also, in the same manner as in Example 1, the base 6 at the 3'-end of the primer consisting of the first probe 61 and the second probe 62 is designed to be brought into the position 35 where the presence or absence of mutation of the target DNA 63 is to be examined. In FIG. 6(b), the complementary strand extension takes place when the primer consisting of the first probe 61 and the second probe 62 is hybridized with the target DNA 63, since base 6 (G) at the 3'-end of the primer and base 35 (C) on the target position of the target DNA are complementary as shown in FIG. 1(a). Namely, this is an example in which the complementary strand extension takes place for the wild type without substitution.

Figure 6C:
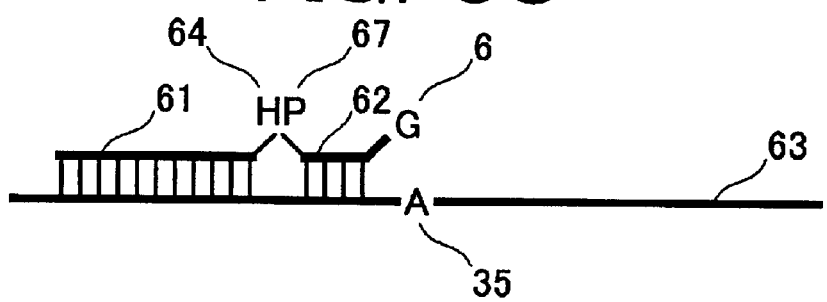

In contrast, FIG. 6(c) illustrates an example in which no complementary strand extension reaction takes place when a primer hybridizes with a mutant DNA having a base substitution. In the example shown in FIG. 6(c), base 6(G) at the 3'-end of the primer and base 35 (A) on the corresponding position of the target DNA are not complementary. Therefore, as explained in FIG. 1(b), no extended complementary strand is formed by the hybridization of the primer. In this Example, unlike the case explained in FIG. 1(b), no extended complementary strand is formed despite that the primer is not complementary, as primer SNP1-2 or SNP1-3 of FIG. 3(a). This is an effect of using the two probes 61 and 62 as a single primer.

Figure 6D:
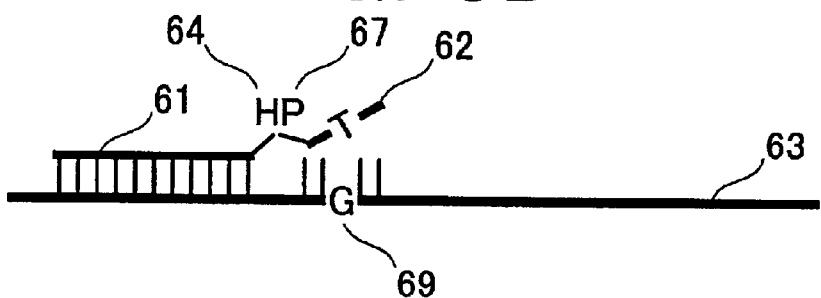

As shown in FIG. 6(d), in this Example 2, hybridization is unstable because the mutation 69 (base G in FIG. (d)) is located on any one of the positions on the target DNA, where the second probe 62 is to be hybridized, and the third base from the 3'-end of the second probe 62 is T. Namely, since the primer consisting of the first probe 61 and the second probe 62 is not stably formed, no extended complementary strand is formed even if base 6 (G) at the 3'-end of the primer and base 35 (C) on the corresponding position on the target DNA are complementary. Again, this is an effect of composing a primer with two probes 61 and 62. In the case where the mutation 69 (G in the example in FIG. 6(d)) exists, it is needless to say that hybridization is stable and an extended complementary strand is formed only when the third base from the 3'-end of the second probe 62 is C in the case where the sequence of site 65 of the target DNA 63 is perfectly complementary to the sequence of the second probe 62, in the example of FIG. 6(d).

Accordingly, the presence or absence of the mutation can be detected by examining the presence or absence of formation of pyrophosphate 68 by examining the presence or absence of photo-emission in the same manner as described in Example 1. Of course, alternatively, the primer 62 can be designed so as to proceed the complementary strand extension reaction only when mutation exists.

Practically, it is preferable to carry out independent reactions using short primers each complementary to wild type and mutant sequences and analyze SNPs or estimate their ratio using the results of the reactions.

Alternatively, the position of mutation is designed to correspond to the 3'-end of the first probe so that the second probe cannot hybridize with the target DNA adjoining close to the first probe if mutation exists.

EXAMPLE 3

In order to examine SNPs, DNA is extracted from a blood sample and stored as a library for use in various tests. Also, the extracted DNA is cleaved into an average length of several kb and the resulting DNA fragments are PCR-amplified and stored as test samples. For various SNP tests, a portion of the stored DNA sample is taken and a necessary short DNA region (100-200b) is again PCR-amplified for use. However, it is too labor-intensive, time-consuming and costly to carry out amplification every time for measurement. Therefore, a method which requires no PCR amplification has been desired. In the present method, a high sensitivity can be attained because a large number of pyrophosphate are produced simultaneously upon the complementary strand extension and used for the chemiluminescence reaction. A complementary strand of about 1 kb is synthesized, and the measurement can be carried out with a sample less than 0.1 fmol and occasionally without PCR. Example 3 is an example in which sensitivity is further improved so that no PCR is required.

In Example 3, extended complementary strands produced in Example 1 and Example 2 are cleaved with an enzyme and the complementary strand extension is again carried out so that further more amounts of pyrophosphate are produced to improve the detection sensitivity.

Figure 7:
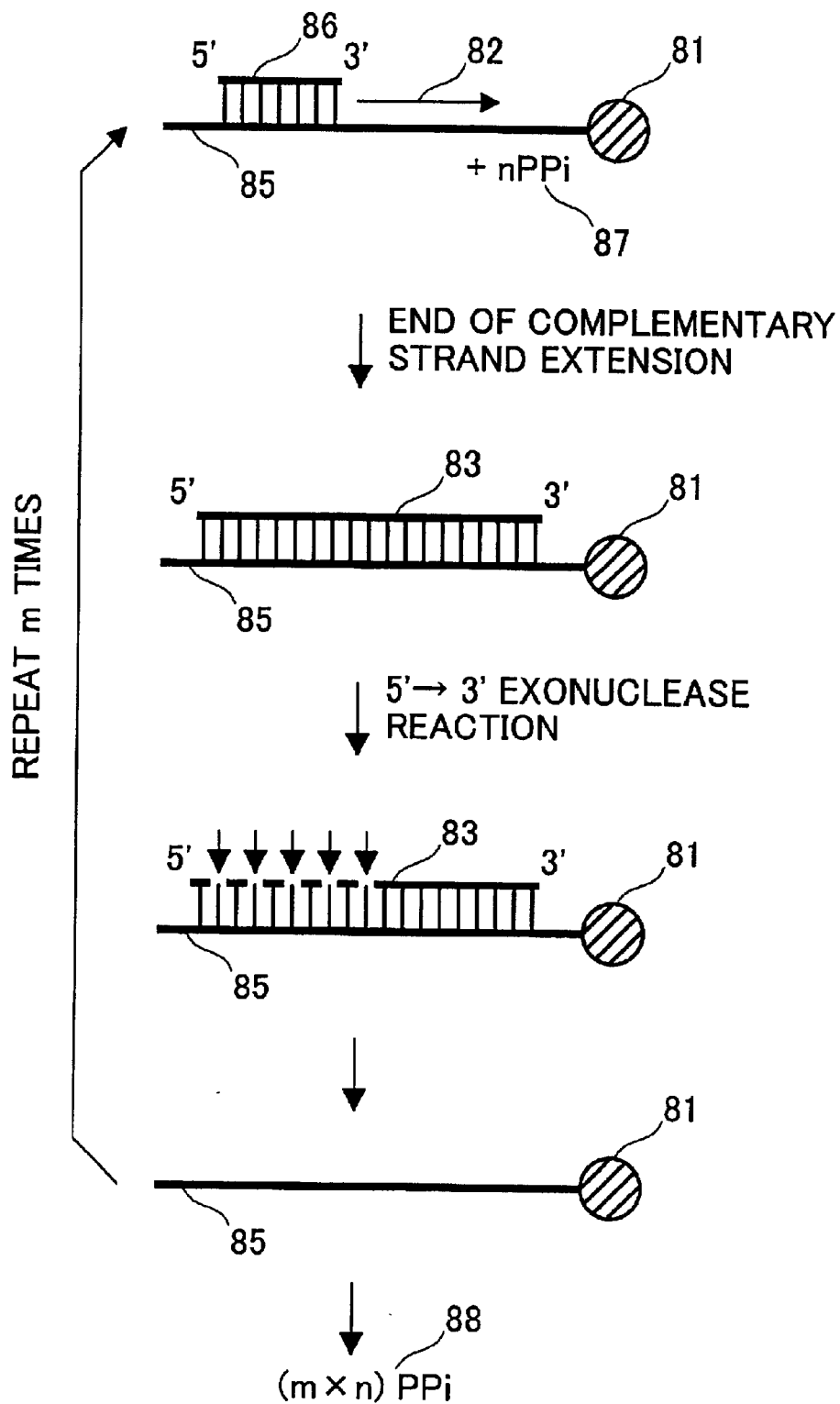
FIG. 7 illustrates Example 3.

FIG. 7 illustrates Example 3. The Figure explains the principle in which the extended complementary strand is cleaved with an enzyme and the complementary strand extension is repeated to produce an enormously large number of pyrophosphate molecules to improve the detection sensitivity.

First, as shown on top of the FIG. 7, a target DNA 85, which is immobilized on a solid carrier 81, such as a bead, at the 5'-end, and a primer 86 are placed with DNA polymerase in a buffer solution. As a result, as explained in FIG. 4(c), pyrophosphate 87 is produced upon the formation of an extended complementary strand 82 of the primer 86. Unlike Example 1, in this Example 3, enzymes for photo-emission are not placed in the buffer solution in the stage of extension of the complementary strand 82 of the primer 86.

Then the complementary strand extension reaction ends when the extension of the complementary strand 82 proceeds to a certain extent, and the complementary strand 83 consisting of the extended complementary strand 82 of the primer 86 and the target DNA 85 form a double-stranded DNA. In this state, exonuclease is put into the buffer solution to cleave the complementary strand. As a result, the complementary strand 83 formed with the extended complementary strand 82 of the primer 86 is decomposed into nucleotides 84 one by one by exonuclease reaction, and ultimately the target DNA 85 is recovered.

Exonucleases to cleave complementary strands will be explained as follows. A 5' 3' exonuclease cuts off nucleotides one by one in the direction from the 5'-end to the 3'-end of a DNA strand while a 3' 5' exonuclease cuts off nucleotides from the 3'-end of a DNA strand. In the case where the match or mismatch of the 3'-end of primer is used to detect the presence or absence of the complementary strand synthesis, the 3' 5' exonuclease is not appropriate because the mismatch site of the primer is cut off and the wild-type and mutant cannot be distinguished. The 5' 3' exonuclease decomposes the DNA stand from the 5'-end of a double-stranded DNA. The 5'-end of the target DNA 85 is immobilized to the solid carrier 81 such as a bead or is modified so that the 5' 3' exonuclease does not decompose the target DNA. The 5' 3' exonuclease is suitable for distinguishing mutation using the mismatch of the 3'-end.

The primer 86 excessibly present in the buffer solution again hybridizes with this target DNA 85 and thus the extended complementary strand 82 of the primer 86 is again formed. Thus, pyrophosphate 87 is newly produced.

Supposing that n molecules of pyrophosphate 87 are produced by the formation of the extended complementary strand 82 of the primer 86 and that the formation of the extended complementary strand 82 and decomposition of the complementary strand 83 by the 5' 3' exonuclease reaction are repeated m times, (m×n) molecules of pyrophosphate 88 are to be produced as a result of the total of m times of formation of the extended complementary strand 82.

After the production of (m×n) molecules of pyrophosphate 88, enzymes for photo-emission are added to the buffer solution. Pyrophosphate 88 is then converted to ATP and the ATP oxidizes luciferin to newly produce pyrophosphate PPi. The newly produced PPi turns into ATP by the action of ATP sulfurylase and again reacts with luciferin. Accordingly, if m=10, namely the repeat is 10 times, the photo-emission by this method is about 10000 times stronger than that by pyrosequencing or the like, since about 1000 molecules of pyrophosphate are produced when one DNA complementary strand is formed.

The formation of the extended complementary strand 82 and decomposition of the complementary strand 83 can be simultaneously proceeded. In this case, DNA polymerase having a 5' exonuclease activity is preferably used.

In the case where the formation of the extended complementary strand 82 and the decomposition of the complementary strand 83 are repeated in the same manner as described above using a 3' 5' exonuclease instead of the abovementioned 5' 3' exonuclease, the primer 86 is modified to have a sulfur bonding at the 3'-end instead of a phosphoric acid bonding. In this way, a nucleotide in the primer, which is complementary to the base at the position to be examined for mutation, can be protected from decomposition and cut-off by the exonuclease. A. DNA polymerase having a strong 3' exonuclease activity is conveniently used.

In either cases, the primer 86 hybridizes with the target DNA 85. The complementary strand extension proceeds or does not proceed according to match or mismatch of the 3-end of the primer 86, which determines the presence or absence of mutation. Mutation can be accurately examined, for example, by modifying the sequence to have an artificial mismatch near the 3'-end of the primer 86, if necessary.

EXAMPLE 4

Example 4 is an example in which a multiple number of primers are used. A simple examination to detect the incidence of formation of the extend complementary strand using a single primer is not satisfactory to determine the type of mutation or to exactly know the kind or the frequency of mutation present in a sample DNA.

Therefore, it is desirable to examine mutations which occur both strands of a double-stranded DNA of interest. It is effective to examine whether an extended complementary strand is formed using a total of four kinds of primers which are complementary to the wild type and mutant of both strands.

Complementary strand extension reactions starting from these four kinds of primers are carried out independently but under the same conditions, and the intensity of the resulting chemiluminescence is compared to obtain information such as the ratio of existing mutation. In order to equalize the reaction conditions, the four kinds or multiple numbers of primers are immobilized on different positions of the solid surface by kind or on different beads by kind and then the complementary strand extension is carried out in the same reaction solution in a spatially separated state. Of course, the reaction can be carried out by placing the primers individually in partitioned small reaction cells. Further, a reaction part can be used, in which the reaction solution can move between the cells while the primers are immobilized on beads or the like and cannot move between the cells. Further, not only the four kinds of primers but also a group of primers corresponding to various SNPs can be examined simultaneously so that various SNPs can be detected simultaneously. Further, genomes of many people can be examined for one or several SNPs. Pyrophosphate produced by the complementary strand extension reaction and chemiluminescence generated through ATP produced from the pyrophosphate are observed discriminately according to the kind of primers.

Figure 8:
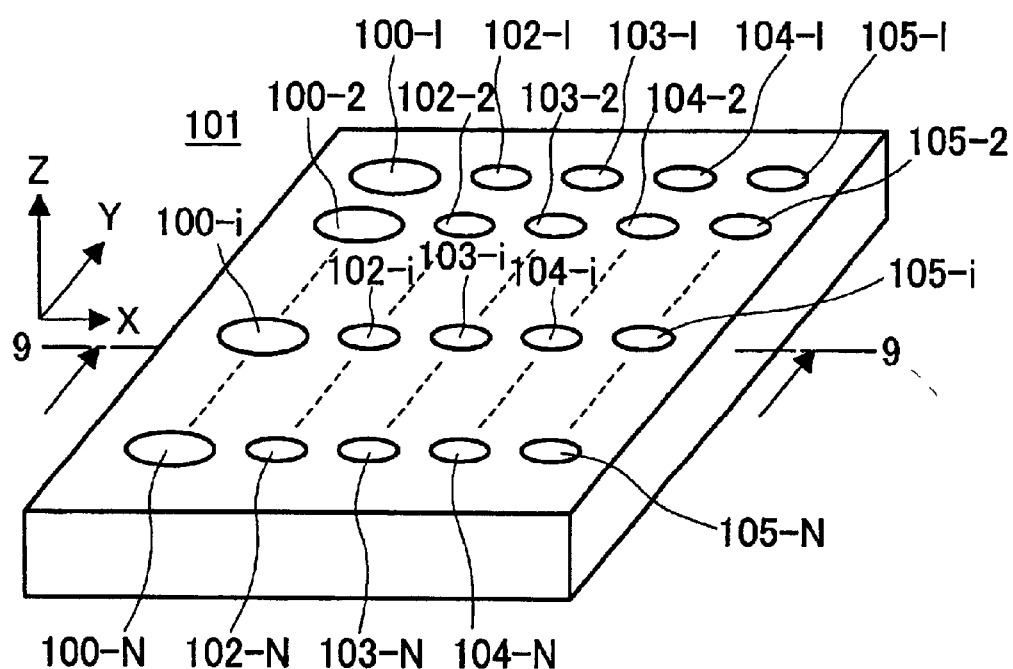
FIG. 8 is a perspective view showing an example of the structure of the DNA mutation detection apparatus of Example 4 of the present invention.
Figure 9:
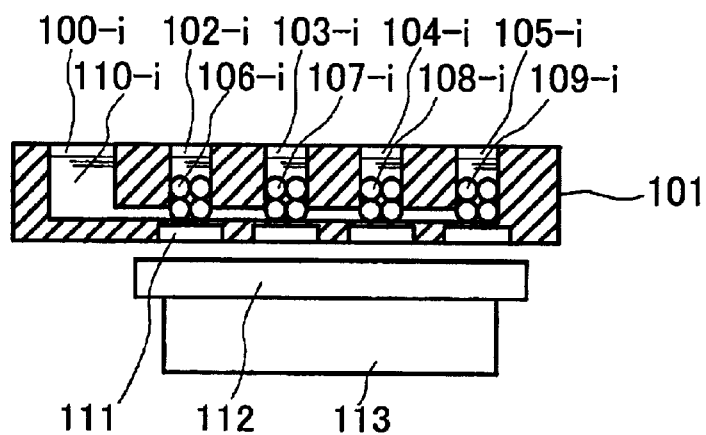
FIG. 9 is a cross-sectional view showing an example of the structure of the DNA mutation detection apparatus of Example 4 of the present invention.

FIGS. 8 and 9 illustrate an example of the structure of the SNP detection apparatus of Example 4. FIG. 8 is a perspective view and FIG. 9 is a cross-sectional view taken on the dotted broken line 9—9 of FIG. 8 viewing in the direction shown with an arrow (Y direction).

In this example, partitioned reaction cells 102-i, 103-i, 104-i, and 105-i (i=1, 2, . . . , N) are formed on a reaction chip 101 having the transparent bottom, and beads 106-i, 107-i, 108-i, and 109-i (i=1, 2, . . . , N) on which primers are immobilized, are held in the cells according to the kind of the primers. On the other hand, reaction fluid cells 100-i (i=1, 2, . . . , N) are formed parallel to the reaction cells 102-i, 103-i, 104-i, and 105-i (i=1, 2, . . . , N). The reaction fluid cells 100 and the reaction cells 102 in corresponding positions are connected at the bottom. Reaction fluids 110-i (i=1, 2, . . . , N) containing a single-stranded target DNA are injected into the reaction fluid cells 100-i (i=1, 2, . . . , N). Since the reaction fluid cells 100 and the reaction cells 102 are connected at the bottom, reaction fluids 110-i (i=1, 2, . . . , N) injected into the reaction fluid cells 100-i (i=1, 2, . . . , N) are supplied into the reaction cells 102-i, 103-i, 104-i, and 105-i (i=1, 2, . . . , N).

Prior to the complementary strand extension reaction, primer-i (i=1, 2, . . . , N) and target DNA-i (i=1, 2, . . . , N) are thoroughly hybridized. After that, a mixed solution of the w four kinds of dNTP is added to each of the reaction cells 100-i (i=1, 2, . . . , N) to start the complementary strand extension reaction.

Chemiluminescence generated as a result of the complementary strand extension reaction is detected using a lens 111 placed at the transparent bottom of the reaction chip 101 or a line sensor or two-dimensional sensor photo-detector 112 through the transparent bottom of the reaction chip 101. In the case where the line sensor 112 is used, the photo-emission is measured by scanning a detector support 113 along the bottom of the reaction chip 101. In the case where the two-dimensional sensor is used, scanning of the detector support 113 is not necessary.

Of course, the abovementioned light-detecting system can be placed on the top of the reaction chip 101. Further, the light can be detected by scanning the bottom or the top surface of the reaction chip 101 using a photon multiplier tube and measuring the photo-emission for every reaction cell in a designated order.

In the SNP detection apparatus shown in FIG. 8 and FIG. 9, multiple kinds of target DNAs can be analyzed simultaneously.

The abovementioned example refers to primers having different kinds of bases at the 3'-end. This system can also be used effectively to detect base substitutions which occur different sites of the target DNA, in which multiple kinds of different primers are prepared and base substitutions on different sites of the target DNA can be collectively detected. In this case, the reaction chip 101 is constructed to have a multiple number, at least the number of the kind of primers, of reaction cells in the X direction.

Further, in order to simplify the structure of the apparatus, the reaction part can be placed on a turntable.

Figure 10:
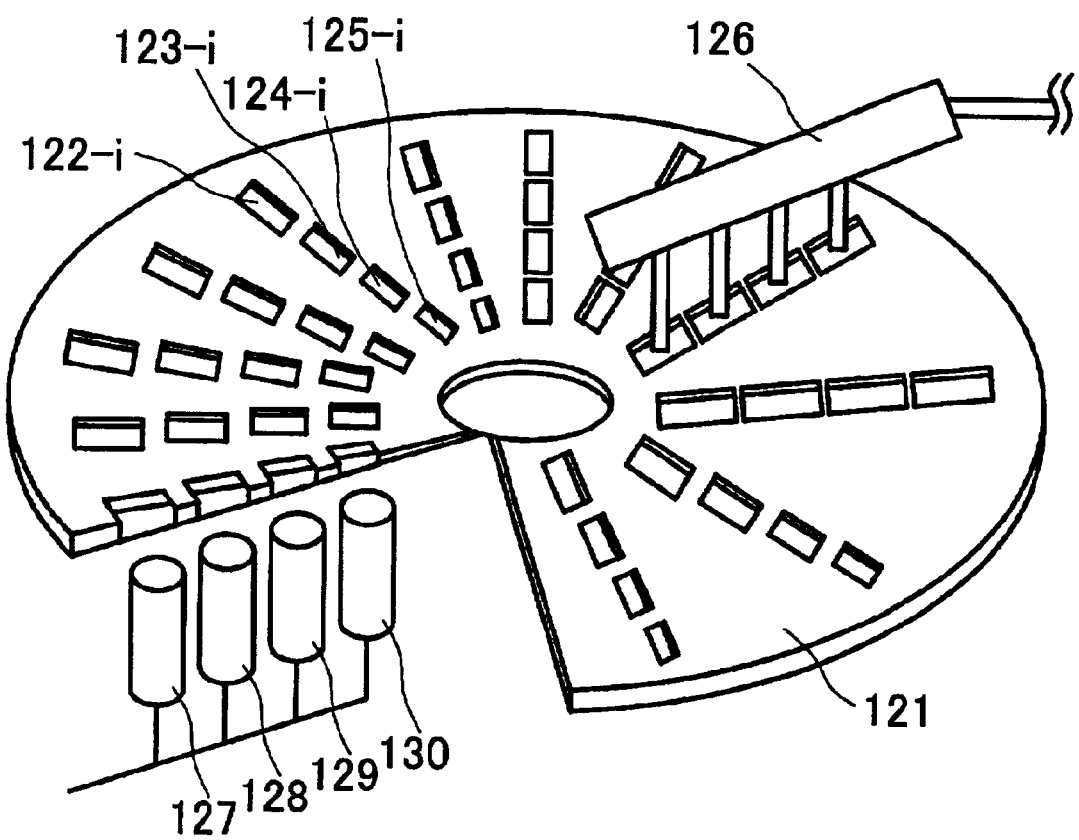
FIG. 10 illustrates another example of the structure of the DNA mutation detection apparatus of Example 4 of the present invention.

FIG. 10 illustrates another embodiment of the structure of the SNP detection apparatus of Example 4. In the structure shown in FIG. 10, four reaction chambers 122-i, 123-i, 124-i, and 125-i having transparent bottoms are held on a round turntable 121 in the radial direction. Beads each having different primers immobilized on the surface are held in the reaction chambers. The bottom areas of the reaction chambers 122-i, 123-i, 124-i, and 125-i are the same.

A multiple number of the reaction chambers 122-i, 123-i, 124-i, and 125-i (i=1, 2, . . . , N) are placed on the round turntable 121 in the peripheral direction. A reaction solution containing a target DNA is added to the reaction chambers 122-i, 123-i, 124-i, and 125-i (i=1, 2, . . . , N) using an injection nozzle 126 having four flow-out openings, and the target DNA is hybridized with the primers immobilized on the beads. Then, a dNTP mixed solution is added and the complementary strand extension proceeds in each reaction chamber.

Chemiluminescence generated as a result of the complementary strand extension is examined one by one for the multiple reaction chambers placed on the turntable 121 in the peripheral direction using photon multiplier tubes 127, 128, 129, and 130 placed under the turntable 121, while the turntable 121 turns.

EXAMPLE 5

In Example 5, the complementary strand extension reaction is carried out by hybridizing the two oligomers illustrated in Example 2 in a series with the target. Mutations are examined by changing the kind of the second oligomer (the second probe illustrated in Example 2) instead of using the four kinds of primers illustrated in Example 4, which are immobilized on a solid.

In a method of Example 5, the first oligomer (the first probe illustrated in Example 2) is immobilized on the surface of solid carriers, such as beads, so that the kinds of primers to immobilize on the solid carriers can be advantageously reduced. The solid carriers on which the first oligomer (probe) is immobilized are placed in the reaction cells or the reaction chambers illustrated in Example 4.

FIG. 11 illustrates an example of the structure of primers, in which a single-stranded DNA derived from the p53 gene, DNA 200, containing the sequence of the exon 8, is used as a target DNA. The DNA 200 has a standard base sequence of 158 base length as shown in SEQ ID NO: 10. Of course, DNA 200 is a DNA strand which contains a 158-base long standard base sequence shown in SEQ ID NO: 10 and the following discussion for the detection of mutations 150, 151, 152, 153, and 154 is applicable also in the case where a base sequence derived from the p53 gene is linked at the 5'-end and/or the 3'-end in addition to the sequence shown in FIG. 11.

```
TGGTAATCTA CTGGGACGGA AACAGCTTTG  SEQ ID NO: 10

AGGTGCGTGT TTGTGCCTGT CCTGGGAGAG

ACCGGCGCAC AGAGGAAGAG AATCTCCGCA

AGAAAGGGGA GCCTCACCAC GAGCTGCCCC

CAGGGAGCAC TAAGCGAGGT AAGCAAGCAG

GACAAGAA
```

Long oligomers 142, 144, 146, and 148 corresponding to mutations are prepared as shown in FIG. 11. Both chains of the double-stranded DNA can be detected to improve the accuracy although only one side of the DNA chains is illustrated in the Figure for simplification. The ends of these long oligomers are treated to be incapable of proceeding the complementary strand extension in the same manner with the first probe 61 shown in FIGS. 6(a), 6(b), 6(c) and 6(d).

Six-base-long oligomers 141, 143, 145, and 147 are prepared to be hybridized with the target DNA adjoining closely to the long oligomers 142, 144, 146, and 148. The 6-base-long oligomers (141, 143, 145, and 147) correspond to the second probe 62 shown in FIGS. 6(b), 6(c), and 6(d). As illustrated in Example 2, the 6-base-long oligomers (141, 143, 145, and 147) alone hybridize with the target DNA and synthesize complementary strands in a low probability, but they can hybridize and synthesize complementary strands when they closely adjoin to the long oligomers 142, 144, 146, and 148.

However, in the case where the 3'-end of the long oligomers 142, 144, 146, and 148 mismatches to the target DNA, or the 3'-end of the 6-base-long oligomers (141, 143, 145, and 147) or either one of the bases in the sequences of the 6-base-long oligomers mismatches to the target DNA, the 6-base-long oligomers do not hybridize with the target DNA. Of course, 5-base-long oligomers can also be used.

In this case, the primers are designed such that the 3'-end of the 6-base-long oligomers comes to the point to be tested for mutation of the target DNA, and the examination is carried out. Not only the presence or absence of mutations but also their ratio can be recognized by synthesizing complementary strands using 6-base-long primers each complementary to the wild type and mutant sequences.

Therefore, the primers are designed such that the 3'-end of the 6-base-long oligomers comes to the point to be tested for mutation of the target DNA, and the examination is carried out. A readiness of occurring the complementary strand extension reaction or the like depending on the kind of bases at the 3'-end of 6-base-long oligomers can also be examined by changing the kind of 6-base-long oligomers.

Actually in the exon 8 of the p53, mutations at positions 150, 151, 152, 153, and 154 indicated with arrows in FIG. 11 can be detected. The mutations at positions 150, 151, 152, 153, and 154 indicated with arrows in FIG. 11 are T A, G A, C T, GC AT, and C T when the substitution of standard base X by base Y is expressed X Y (in which X and Y are either A, T, G, or C).

FIG. 12 shows structures of probes which are incapable of proceeding the complementary strand extension and 6-base-long primers for the detection of the mutations shown in FIG. 11.

The probe 142 incapable of proceeding the complementary strand extension binds complementarily to the region from position 43 to 58 from the 5'-end of the sequence of SEQ ID NO: 10 and has the 16-base-long sequence of SEQ ID NO: 11. Of course, the probe 142 can be a 20- to 30-base-long oligomer. N is a base, either G or T, corresponding to the wild type or mutant sequence.

CTCCCANGAC AGGCAC (SEQ ID NO: 11)

The 6-base-long primer 141 binds complementarily to the region from position 37 to 42 from the 5'-end of the sequence of SEQ ID NO: 10 and has the 6-base-long sequence of SEQ ID NO: 11. N is either A or T.

NAACAC (SEQ ID NO: 11')

It is understood that the mutation 150 exists if signal is obtained when N=T and not when N=A.

The probe 144 incapable of proceeding the complementary strand extension binds complementarily to the region from position 58 to 72 from the 5'-end of the sequence of SEQ ID NO: 10 and has the 16-base-long sequence of SEQ ID NO: 12. The probe can have any base length as long as the length is sufficient for stable hybridization, and thus longer oligomer can be used if necessary. N at eleventh base from 5' terminal is G or A, and NN at sixth to seventh base from 5' terminal is GC or AT.

TCTGTNNGCC NGTCTC (SEQ ID NO: 12)

The 6-base-long primer 143 binds complementarily to the region from position 52 to 57 from the 5'-end of the sequence of SEQ ID NO: 10 and has the 6-base-long sequence of SEQ ID NO: 12'. N is either T or G.

TCCCAN (SEQ ID NO: 12')

The probe 146 incapable of proceeding the complementary strand extension binds complementarily to the region from position 69 to 84 from the 5'-end of the sequence of SEQ ID NO: 10 and has the 16-base-long sequence of SEQ ID NO: 13.

GTTTCTCTTC CTCTGT (SEQ ID NO: 13)

The 6-base-long primer 145 binds complementarily to the region from position 63 to 68 from the 5'-end of the sequence of SEQ ID NO: 10 and has the 6-base-long sequence of SEQ ID NO: 13'. N at 3' terminal is G or A, and NN at the first and second bases from 5' terminal is GC or AT.

NNGCCN (SEQ ID NO: 13')

In order to discriminate mutations of different positions, four primers including ones for the wild type are prepared (eight primers if both chains of the double-stranded DNA are to be examined). Primers corresponding to the wild type sequence can be used as a mixture when only the presence or absence of mutation is to be examined. Of course, one or more mutations can be detected one by one by shifting the positions of the primers which bind complementarily to the target DNA.

The probe 148 incapable of proceeding the complementary strand extension binds complementarily to the region from position 141 to 156 from the 5'-end of the sequence of SEQ ID NO: 10 and has the 16-base-long sequence of SEQ ID NO: 14.

CTTGTCCTGC TTCGTT (SEQ ID NO: 14)

The 6-base-long primer 147 binds complementarily to the region from position 135 to 140 from the 5'-end of the sequence of SEQ ID NO: 10 and has the 6-base-long sequence of SEQ ID NO: 14'. N is either G or A.

ACCTCN (SEQ ID NO: 14')

If N=A, the presence of the mutation 154 can be detected.

Of course, the SNP detection apparatus illustrated in Example 4 can be used for the detection of mutations illustrated in Examples above.

As illustrated above, according to the present invention, the number of pyrophosphate molecules produced at a time can be increased by simultaneously adding the four kinds of dNTP to the reaction part to proceed the complementary strand extension, and the resulting photo-emission intensity can be increased by several orders higher than that obtained by the conventional pyrosequencing method, by repeating the pyrophosphate production process.

Accordingly, the presence or absence of the target DNA and the presence or absence of mutations can be examined without the need for an amplifying process such as PCR. Further, when the wild type and mutant are present in the target DNA at a certain ratio, various base substitutions can be examined by using respectively corresponding primers each immobilized on the surface of different solid carriers. In particular, substitutions on multiple sites contained in a long DNA can be discriminated. The method of the present invention can be applicable to a high throughput apparatus to simultaneously analyze a multiplicity of DNA samples, for example, by immobilizing the target DNAs on beads or on partitioned solid surface.

Characteristics of mutation (SNP) detection methods of the present invention are listed as follows.

In a mutation detection method of the present invention, a primer, which has a sequence complementary to a region of a specific DNA sequence or a region of a specific RNA sequence to be detected, hybridizes with a DNA sample or an RNA sample and whether a complementary strand extension reaction with nucleic acid substrates (dATP, dTTP, dGTP and dCTP, or analogues thereof) using DNA polymerase in the case of DNA sample or reverse transcriptase in the case of RNA samples proceed or not is detected by converting pyrophosphate produced as a reaction by-product of the complementary strand extension into ATP, carrying out a photo-emission reaction using luciferase or the like and detecting the resulting photo-emission, whereby the presence or absence of the specific sequence is detected.

In the complementary strand extension reaction using a primer which directly hybridizes with the RNA sample, four kinds of nucleic acid substrates, and reverse transcriptase, cDNA is formed and at this moment RNA mutations can be detected by detecting dissociating pyrophosphate.

In the abovementioned method, in addition to the primer which hybridizes with the specific sequence, multiple kinds of nucleic acid substrates are simultaneously added, the complementary strand extension reaction is repeated, the resulting pyrophosphate is converted into ATP, and thereby a photo-emission reaction is carried out to detect the photo-emission. Further, in addition to the primer which hybridizes with the specific sequence, four kinds of nucleic acid substrates are simultaneously added, the complementary strand extension proceeds, the resulting ATP is converted into pyrophosphate, and a photo-emission reaction is carried out for photo-emission detection.

Further in the abovementioned method, a nucleotide which is not complementary to the target DNA or the target RNA is artificially inserted in the vicinity of the 3'-end of the primer, the resulting pyrophosphate is converted into ATP, and a photo-emission reaction is carried out with a photo-emission reagent such as luciferin using luciferase or the like to detect the photo-emission, whereby SNPs are detected by examining whether the complementary strand extension is proceeded or not.

Further, in the abovementioned method, the complementary strand synthesis and chemiluminescence detection are each independently carried out using at least two kinds of primers, which are capable of hybridizing with wild type and mutant sequences and proceeding the complementary strand synthesis, and the presence or absence and the ratio of mutation can be accurately determined using the resultant information. Further, the abovementioned two kinds of primers are prepared for each of a double-stranded DNA (totally four kinds), and the complementary strand synthesis and photo-emission detection are carried out to accurately determine the ratio of mutation. This is effective when a correlation between diseases and SNPs is to be statistically studied for a sample which is a mixture of various genome DNAs.

Further, in the abovementioned method, the extended complementary strand by the complementary strand extension reaction is decomposed from its ends by an enzyme and the primers repeatedly hybridize with a target DNA or a target RNA to repeatedly proceed the complementary strand extension reaction, and a multiplicity of PPi produced by a series of repeated complementary strand extension reaction are converted into ATP, which is reacted with luciferin to generate photo-emission to be detected. The enzyme to decompose the extended complementary strand is one which decomposes a DNA strand or RNA strand from the 5'-end.

Further, in the abovementioned method, the complementary strand extension is carried out using a primer which is complementary to a target DNA strand or RNA strand and the 3'-end of which is bound to targeted two-base substitution site or its vicinity, pyrophosphate resulting from the complementary strand extension is converted into ATP or the like, and a reaction with a photo-emitting substrate such as luciferin is carried out to generate chemiluminescence to detect SNPs.

A reagent kit of the present invention for detecting SNPs or examining the SNP ratio at least includes a primer, which is complementary to a target DNA strand or RNA strand and the 3'-end of which is bound to a targeted single base substitution site or its vicinity, and nucleic acid substrates (dATP, dTTP, dGTP, and dCTP, or analogues thereof).

Further, a reagent kit of the present invention for detecting SNPs or examining the SNP ratio at least includes a primer, which is complementary to a target DNA strand or RNA strand and the 3'-end of which is bound to a targeted single base substitution site or its vicinity, nucleic acid substrates (dATP, dTTP, dGTP, and dCTP, or analogues thereof), and an enzyme which decomposes pyrophosphate contained as an impurity.

In the method for detecting SNPs of the present invention, primers having different kinds of nucleotides at their ends are held separately by kind of the primers in different cells on the solid surface or in different reaction chambers, and a mixture of multiple kinds of dNTP is added to the cells or a reaction solution of the reaction chambers to provide conditions where the complementary strand extension reaction starting from the primers can take place, pyrophosphate produced as a result of actual complementary strand extension reaction starting from the primers which hybridize with a target DNA or a target RNA is converted into ATP, and chemiluminescence produced by reacting the ATP with luciferin or the like is detected to discriminate the kind of primers which are engaged in the complementary strand extension reaction, whereby mutations in the target DNA or target RNA are detected.

Further, in the method for detecting SNPs of the present invention, multiple kinds of long oligomers, which are different in sequence from each other and are capable of hybridizing with a target DNA or a target RNA but incapable of proceeding the complementary strand extension reaction, are held separately by kind of the long oligomers in different cells on the solid surface or in different reaction chambers, 5-base-long to 8-base-long short oligomers capable of proceeding the complementary strand extension reaction are added to the cells or the reaction chambers, the short oligomers and said long oligomers are serially hybridized with the target. DNA or the target RNA, the complementary strand extension reaction starting from the short primers proceeds by further adding a mixture of multiple kinds of dNTP, pyrophosphate produced as a result of the reactions is converted into ATP, and chemiluminescence produced by reacting the ATP with luciferin or the like is detected to discriminate the kind of the primers which are engaged in the complementary strand extension reaction, whereby mutations in the target DNA or the target RNA are detected. In this case, the chemiluminescence reagent is not limited to luciferin.

A mutation detection apparatus of the present invention comprises a reaction chip furnished with multiple cells on the solid surface, which holds primers differing in kinds of end nucleotides from each other, separately by kind of primers, or a reaction chamber supporting base on which multiple reaction chambers holding the primers separately by kind are placed; and a light detector to detect chemiluminescence which is produced by reacting ATP with luciferin or the like; said ATP being converted from pyrophosphate produced as a result of actual complementary strand extension reaction starting from the primers hybridized with a target DNA or a target RNA under the conditions where the complementary strand extension reaction starting from the primers can take place by adding a mixture of multiple kinds of dNTP to the cells or a reaction solution in the reaction chambers, whereby the kind of primers which are engaged in the complementary strand extension reaction is discriminated to detect mutations contained in the target DNA or the target RNA.

A mutation detection apparatus of the present invention for detecting mutations in a target DNA or a target RNA comprises a reaction chip furnished with multiple cells on the solid surface, which hold multiple kinds of long oligomers, which are capable of hybridizing with the target DNA or the target RNA but incapable of being engaged in the complementary strand extension and are different in sequence from each other, separately by kind of the oligomers, or a reaction chamber supporting base on which multiple reaction chambers holding the long oligomers separately by kind of the oligomers are placed; and a light detector to detect chemiluminescence which is produced by reacting ATP with luciferin or the like; said ATP being converted from pyrophosphate produced by a serial hybridization of short oligomers and the long oligomers with the target DNA or the target RNA by adding 5-base-long to 8-base-long short oligomers capable of being engaged in the complementary strand extension reaction respectively to the cells or the reaction chambers, followed by the subsequent complementary strand extension reaction starting from the short primers by further adding a mixture of multiple kinds of dNTP, whereby the kind of the short primers which are engaged in the complementary strand extension reaction is discriminated to detect mutations contained in the target DNA or the target RNA Further, a method for detecting mutations according to the present invention comprises a step of hybridizing a primer which contains a sequence complementary to a region of a specific sequence of a target DNA or a target RNA; a step of carrying out the complementary strand extension reaction starting from the primer using four kinds of nucleic acid substrates and polymerase or reverse transferase; and a step of detecting photo-emission in which pyrophosphate produced as a reaction by-product of the complementary strand extension reaction is converted into ATP and a photo-emission reaction is carried out using an enzyme, whereby the presence or absence of the specific sequence is detected.

Further, a method for detecting mutations according to the present invention comprises a step of hybridizing a primer which contains a sequence complementary to a region of a specific sequence of a target DNA or a target RNA and a sequence not complementary to the sequence of the target DNA or the target RNA at the second base or the third base from the 3'-end; a step of carrying out the complementary strand extension reaction starting from the primer using four kinds of nucleic acid substrates and polymerase or reverse transferase; and a step of detecting photo-emission in which pyrophosphate produced as a reaction by-product of the complementary strand extension reaction is converted into ATP and a photo-emission reaction is carried out using an enzyme, whereby the presence or absence of the specific sequence is detected.

Further, a method for detecting mutations according to the present invention comprises a step of serially hybridizing a 5-base-long to 8-base-long short oligomer, which is capable of being engaged in the complementary strand extension reaction, and a long oligomer, which is capable of hybridizing with a target DNA or a target RNA but incapable of being engaged in the complementary strand extension reaction, with the target DNA or the target RNA; a step of carrying out the complementary strand extension reaction starting from the short primer using four kinds of nucleic acid substrates and polymerase or reverse transferase; and a step of detecting photo-emission, in which pyrophosphate produced as a reaction by-product of the complementary strand extension reaction is converted into ATP and the photo-emission reaction is carried out using an enzyme, whereby the presence or absence of the specific sequence is detected.

A detection method of the present invention uses two probes (primers) each corresponding to target wild type and mutant sequences to improve accuracy, and its use is not limited to the detection of pyrophosphate produced as a result of the complementary strand synthesis. Products, i.e., DNA strands, can be labeled with different labeling fluorescent substances and analyzed for comparison by electrophoresis or the like. Further, the method can be applied to other SNP detection methods. Namely, a pair of probes, one acting on a wild type sequence and the other acting on the mutant sequence to generate signals, are effectively used to accurately measure the ratio of mutation.

As illustrated above, according to the present invention, mutation can be readily detected with great accuracy by (1) using primers which are specifically designed considering the presence or absence of mutations contained in DNAs, (2) judging whether the primers form extended complementary strands by the complementary extension reaction; and (3) increasing the number of pyrophosphate molecules released by the complementary strand extension reaction by two orders greater than that obtained using the conventional pyrosequencing, in the detection of the extended complementary strand. Further, the mutation ratio in multiple samples containing wild type and mutant sequences can be accurately examined by the use of multiple probes or primers.

Further, according to the present invention, DNA samples containing multiple kinds of DNA mutations can be analyzed. Namely, various information required for DNA mutation measurements (e.g., whether only an anticipated base sequence exists, whether a mutation exists, what kind of mutations appears and where mutations appear, or how many sites mutations appear) can be readily obtained by examining the mutations using multiple kinds of primers taking the anticipated base sequences into consideration.

The present invention can provide a method and an apparatus for detecting DNA mutations without the need for gel electrophoresis, in which no emission light resource is necessary because of its high sensitivity, and engaging reactions are simple and quick, and further a method and an apparatus for detecting DNA mutations, in which a sample containing multiple mutations can be analyzed with great accuracy. Accordingly, various information required for DNA mutation measurements can be readily obtained.

What is claimed is:

1. A method for detecting nucleic acid mutation comprising:

hybridizing a primer, containing a complementary sequence complementary to a region of a specific sequence of target nucleic acid and a base not complementary to the target nucleic acid at second base or third base from 3' end of the primer, with the target nucleic acid;

performing complementary strand extension reaction from the primer using polymerase, plurality of nucleic acid substrates and the primer;

generating chemoluminiscence using ATP and an enzyme, the ATP converted from pyrophosphate generated as by-product of the complementary strand extension reaction; and detecting the chemoluniniscence generated in the step of generating chemoluninscence wherein the specific sequence of target nucleic acid is related to mutation of the nucleic acid and presence or absence of the specific sequence of target nucleic acid is detected;

wherein extended complementary strand generating in the step of performing complementary strand extension reaction is decomposed with an enzyme, the primer being repeatedly hybridized with the target nucleic acid to perform the complementary strand extension reaction.

2. A method for detecting nucleic acid mutation comprising:

hybridizing a primer, containing a complementary sequence complementary to a region of a specific sequence of target nucleic acid and a base not complementary to the target nucleic acid at second base or third base from 3' and of the primer, with the target nucleic acid;

performing complementary strand extension reaction from the primer using polymerase, plurality of nucleic acid substrates and the primer;

generating chemoluniscence using ATP and an enzyme, the ATP converted from pyrophosphate generated as by-product of the complementary strand extension reaction; and detecting the chemoluminiscence generated in the step of generating chemoluniscence wherein the specific sequence of target nucleic acid is related to mutation of the nucleic acid and presence or absence of the specific sequence of target nucleic acid is detected;

wherein extended complementary strand generating in the step of performing complementary strand extension reaction is decomposed with an enzyme, the primer being repeatedly hybridized with the target nucleic acid to perform the complementary strand extension reaction; and wherein the enzyme decompose the extended complementary strand from 5' end of the extended complementary strand.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence

```
<220> FEATURE:
<223> OTHER INFORMATION: DNA primer used for forming an extended
      complementary strand

<400> SEQUENCE: 1
agttttaaga gggttgttgt                                                    20

<210> SEQ ID NO 2
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 2
agttttaaga gggttgttgc                                                    20

<210> SEQ ID NO 3
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 3
agttttaaga gggttgttgg                                                    20

<210> SEQ ID NO 4
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 4
agttttaaga gggttgttga                                                    20

<210> SEQ ID NO 5
<211> LENGTH: 20
<212> TYPE: DNA
<213> ORGANISM: Artificial Sequence
<220> FEATURE:
<223> OTHER INFORMATION: DNA primer having base sequence replaced T at
      18 of SEQ ID NO: 1 by A for introducing a mismatch between DNA
      primer and template DNA

<400> SEQUENCE: 5
agttttaaga gggttgtagt                                                    20

<210> SEQ ID NO 6
<211> LENGTH: 20
<212> TYPE: DNA
<213> ORGANISM: Artificial Sequence
<220> FEATURE:
<223> OTHER INFORMATION: DNA primer having base sequence replaced T at
      18 of SEQ ID NO: 2 by A for introducing a mismatch between DNA
      primer and template DNA

<400> SEQUENCE: 6
agttttaaga gggttgtagc                                                    20

<210> SEQ ID NO 7
<211> LENGTH: 20
<212> TYPE: DNA
```

```
<213> ORGANISM: Artificial Sequence
<220> FEATURE:
<223> OTHER INFORMATION: DNA primer having base sequence replaced T at
      18 of SEQ ID NO: 3 by A for introducing a mismatch between DNA
      primer and template DNA

<400> SEQUENCE: 7
agttttaaga gggttgtagg                                                20

<210> SEQ ID NO 8
<211> LENGTH: 20
<212> TYPE: DNA
<213> ORGANISM: Artificial Sequence
<220> FEATURE:
<223> OTHER INFORMATION: DNA primer having base sequence replaced T at
      18 of SEQ ID No: 4 by A for introducing a mismatch between DNA
      primer and template DNA

<400> SEQUENCE: 8
agttttaaga gggttgtaga                                                20

<210> SEQ ID NO 9
<211> LENGTH: 20
<212> TYPE: DNA
<213> ORGANISM: Artificial Sequence
<220> FEATURE:
<223> OTHER INFORMATION: Template DNA

<400> SEQUENCE: 9
tcaaaattct cccaacaaca                                                20

<210> SEQ ID NO 10
<211> LENGTH: 158
<212> TYPE: DNA
<213> ORGANISM: Artificial Sequence
<220> FEATURE:
<223> OTHER INFORMATION: Template DNA originating from p53 and including
      base sequence of exon 8

<400> SEQUENCE: 10
tggtaatcta ctgggacgga aacagctttg aggtgcgtgt ttgtgcctgt cctgggagag    60
accggcgcac agaggaagag aatctccgca agaaagggga gcctcaccac gagctgaaaa   120
cagggagcac taagcgaggt aagcaagcag gacaagaa                           158

<210> SEQ ID NO 11
<211> LENGTH: 16
<212> TYPE: DNA
<213> ORGANISM: Artificial Sequence
<220> FEATURE:
<221> NAME/KEY: unsure
<222> LOCATION: (7)
<223> OTHER INFORMATION: DNA probe complementary with base sequence
      between 43 and 58 of SEQ ID NO: 10 (n is a or c or g or t) and DNA
      probe being not able to be extended

<400> SEQUENCE: 11
ctcccangac aggcac                                                    16

<210> SEQ ID NO 12
<211> LENGTH: 16
<212> TYPE: DNA
<213> ORGANISM: Artificial Sequence
<220> FEATURE:
<221> NAME/KEY: unsure
<222> LOCATION: (6)-(7), (11)
<223> OTHER INFORMATION: DNA probe complementary with base sequence
      between 58 and 72 of SEQ ID NO: 10 (the base sequences of nn at 6
```

-continued

```
      to 7 and the base sequence of n at 11th position from 5' terminal
      is g or a.) and DNA probe being ot able to extended

<400> SEQUENCE: 12
tctgtnngcc ngtctc                                                    16

<210> SEQ ID NO 13
<211> LENGTH: 16
<212> TYPE: DNA
<213> ORGANISM: Artificial Sequence
<220> FEATURE:
<223> OTHER INFORMATION: DNA probe complementary with base sequence
      between 69 and 84 of SEQ ID NO: 10 and DNA probe being not able to
      be extended

<400> SEQUENCE: 13
gtttctcttc ctctgt                                                    16

<210> SEQ ID NO 14
<211> LENGTH: 16
<212> TYPE: DNA
<213> ORGANISM: Artificial Sequence
<220> FEATURE:
<223> OTHER INFORMATION: DNA probe complementary with base sequence
      between 141 and 156 of SEQ ID NO: 10 and DNA probe being not able
      to be extended

<400> SEQUENCE: 14
cttgtcctgc ttcgtt                                                    16
```